(12) United States Patent
Duggan et al.

(10) Patent No.: US 6,472,403 B2
(45) Date of Patent: *Oct. 29, 2002

(54) αV INTEGRIN RECEPTOR ANTAGONISTS

(75) Inventors: Mark E. Duggan, Schwenksville, PA (US); Wasyl Halczenko, Lansdale, PA (US); John H. Hutchinson, Philadelphia, PA (US); Aiwen Li, Audubon, PA (US); Robert S. Meissner, Schwenksville, PA (US); James J. Perkins, Churchville, PA (US); Thomas G. Steele, Schwenksville, PA (US); Jiabing Wang, Chalfont, PA (US); Michael A. Patane, Billerica, MA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/766,148

(22) Filed: Jan. 19, 2001

(65) Prior Publication Data
US 2002/0037889 A1 Mar. 28, 2002

Related U.S. Application Data

(60) Provisional application No. 60/177,168, filed on Jan. 20, 2000.

(51) Int. Cl.[7] ................... A61K 31/44; C07D 498/02; C07D 239/02; C07D 471/02; C07D 491/00
(52) U.S. Cl. ................... 514/300; 514/230.05; 514/333; 544/105; 544/335; 546/81; 546/82; 546/122; 546/115; 546/118; 546/256; 548/306.1; 540/577
(58) Field of Search ............... 514/300, 230.5, 514/333; 544/105, 335; 546/81, 82, 122, 256, 115, 118; 548/306.1; 540/577

(56) References Cited

U.S. PATENT DOCUMENTS

| | | | |
|---|---|---|---|
| 5,981,546 A | 11/1999 | Duggan et al. | 514/300 |
| 6,017,926 A | 1/2000 | Askew et al. | 514/300 |
| 6,066,648 A | 5/2000 | Duggan et al. | 514/300 |
| 6,090,944 A | 7/2000 | Hutchinson | 546/122 |

FOREIGN PATENT DOCUMENTS

| | | |
|---|---|---|
| WO | 0 796 855 A1 | 9/1997 |
| WO | WO 98/08840 | 5/1998 |
| WO | WO 98/18460 | 5/1998 |
| WO | WO 99/30709 | 6/1999 |
| WO | WO 99/30713 | 6/1999 |
| WO | WO 99/31099 | 6/1999 |
| WO | WO 00/09503 | 2/2000 |
| WO | WO 00/78317 A1 | 12/2000 |

OTHER PUBLICATIONS

Duggan et al., "Ligands to the integrin receptor αvβ3", Expert Opinion on Therapeutic Patents, vol. 10, pp. 1367–1383 (2000).

Miller et al., "Identification and in vivo efficacy of small-—molecule antagonists of integrin αvβ3 (the vitronectrin receptor)", Drug Discovery Today, vol. 5, pp. 397–408 (2000).

Gowen et al., "Emerging therapies for osteoporosis", Emerging Drugs, vol. 5, pp. 1–43 (2000).

Kerr et al, "Small molecule αv integrin antagonists: novel anticancer agents", Expert Opinion on Investigational Drugs, vol. 9, pp. 1271–1279 (2000).

Hartman et al., "αvβ3Integrin antagonists as inhibitors of bone resorption", Expert Opinion on Investigational Drugs, vol. 9, pp. 1281–1291 (2000).

*Primary Examiner*—Mukund J. Shah
*Assistant Examiner*—Tam Thom N. Truong
(74) *Attorney, Agent, or Firm*—Patricia A. Shatynski; Mark R. Daniel

(57) ABSTRACT

The present invention relates to novel imidazolidinone derivatives thereof, their synthesis, and their use as αv integrin receptor antagonists. More particularly, the compounds of the present invention are antagonists of the integrin receptors αvβ3 and/or αvβ5 and are useful for inhibiting bone resorption, treating and preventing osteoporosis, and inhibiting vascular restenosis, diabetic retinopathy, macular degeneration, angiogenesis, atherosclerosis, inflammation, inflammatory arthritis, viral disease, cancer, and metastatic tumor growth.

14 Claims, No Drawings

αV INTEGRIN RECEPTOR ANTAGONISTS

CROSS-REFERENCE TO RELATED APPLICATIONS

The present invention is related to U.S. provisional application Ser. No. 60/177,168, filed Jan. 20, 2000, the contents of which are hereby incorporated by reference.

FIELD OF THE INVENTION

The present invention relates to imidazolidinone derivatives, their synthesis, and their use as αv integrin receptor antagonists. More particularly, the compounds of the present invention are antagonists of the integrin receptors αvβ3, αvβ5, and αv integrin receptors associated with other β-subunits, and are useful for inhibiting bone resorption, treating and/or preventing osteoporosis, and inhibiting vascular restenosis, diabetic retinopathy, macular degeneration, angiogenesis, atherosclerosis, inflammatory arthritis, cancer, and metastatic tumor growth.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane receptors through which cells attach and communicate with extracellular matrices and other cells. (See S. B. Rodan and G. A. Rodan, "Integrin Function In Osteoclasts," *Journal of Endocrinology*, 154: S47–S56 (1997), which is incorporated by reference herein in its entirety).

In one aspect of the present invention, the compounds herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin on osteoclasts, e.g., on rat, chicken, mouse and human osteoclasts, is an integrin receptor known as αvβ3, which is thought to interact in bone with matrix proteins that contain the RGD sequence. Antibodies to αvβ3 block bone resorption in vitro indicating that this integrin plays a key role in the resorptive process. There is increasing evidence to suggest that αvβ3 ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, αvβ3 ligands have been found to be useful in treating and/or inhibiting restenosis (i.e. recurrence of stenosis after corrective surgery on the heart valve), atherosclerosis, diabetic retinopathy, macular degeneration, and angiogenesis (i.e. formation of new blood vessels), and inhibiting viral disease. Moreover, it has been postulated that the growth of tumors depends on an adequate blood supply, which in turn is dependent on the growth of new vessels into the tumor; thus, inhibition of angiogenesis can cause tumor regression in animal models (See *Harrison's Principles of Internal Medicine*, 12th ed., 1991, which is incorporated by reference herein in its entirety). Therefore, αvβ3 antagonists which inhibit angiogenesis can be useful in the treatment of cancer by inhibiting tumor growth (See, e.g., Brooks et al., *Cell*, 79:1157–1164 (1994), which is incorporated by reference herein in its entirety).

Evidence has also been presented suggesting that angiogenesis is a central factor in the initiation and persistence of arthritic disease, and that the vascular integrin αvβ3 may be a preferred target in inflammatory arthritis. Therefore, αvβ3 antagonists which inhibit angiogenesis may represent a novel therapeutic approach to the treatment of arthritic disease, such as rheumatoid arthritis (see C. M. Storgard, et al., "Decreased angiogenesis and arthritic disease in rabbits treated with an αvβ3 antagonist," *J. Clin. Invest.*, 103: 47–54 (1999), which is incorporated by reference herein in its entirety).

Moreover, compounds of this invention can also inhibit neovascularization by acting as antagonists of the integrin receptor, αvβ5. A monoclonal antibody for αvβ5 has been shown to inhibit VEGF-induced angiogenesis in rabbit cornea and the chick chorioallantoic membrane model (See M. C. Friedlander, et al., *Science* 270: 1500–1502 (1995), which is incorporated by reference herein in its entirety). Thus, compounds that antagonize αvβ5 are useful for treating and preventing macular degeneration, diabetic retinopathy, cancer, and metastatic tumor growth.

Additionally, compounds of the instant invention can inhibit angiogenesis and inflammation by acting as antagonists of αv integrin receptors associated with other β subunits, such as αvβ6 and αvβ8 (See, for example, Melpo Christofidou-Solomidou, et al., "Expression and Function of Endothelial Cell αv Integrin Receptors in Wound-Induced Human Angiogenesis in Human Skin/SCID Mice Chimeras," *American Journal of Pathology*, 151: 975–83 (1997) and Xiao-Zhu Huang, et al., "Inactivation of the Integrin β6 Subunit Gene Reveals a Role of Epithelial Integrins in Regulating Inflammation in the Lungs and Skin," *Journal of Cell Biology*, 133: 921–28 (1996), which are incorporated by reference herein in their entirety).

In addition, certain compounds of this invention antagonize both the αvβ3 and αvβ5 receptors. These compounds, referred to as "dual αvβ3/αvβ5 antagonists," are useful for inhibiting bone resorption, treating and preventing osteoporosis, and inhibiting vascular restenosis, diabetic retinopathy, macular degeneration, angiogenesis, atherosclerosis, inflammatory arthritis, cancer, and metastatic tumor growth.

Peptidyl as well as peptidomimetic antagonists of the αvβ3 integrin receptor have been described both in the scientific and patent literature. For example, reference is made to W. J. Hoekstra and B. L. Poulter, *Curr. Med. Chem.* 5: 195–204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; WO 00/03973; EP 853084; EP 854140; EP 854145; U.S. Pat. Nos. 5,204,350; 5,217,994; 5,639,754; 5,741,796; 5,780,426; 5,929,120; 5,952,341; 6,017,925; and 6,048,861. Evidence of the ability of αvβ3 integrin receptor antagonists to prevent bone resorption in vitro and in vivo has been presented (see V. W. Engleman et al., "A Peptidomimetic Antagonist of the αvβ3 Integrin Inhibits Bone Resorption In Vitro and Prevents Osteoporosis In Vivo," *J. Clin. Invest.* 99: 2284–2292 (1997); S. B. Rodan et al., "A High Affinity Non-Peptide αvβ3 Ligand Inhibits Osteoclast Activity In Vitro and In Vivo," *J. Bone Miner. Res.* 11: S289 (1996); J. F. Gourvest et al., "Prevention of OVX-Induced Bone Loss With a Non-peptidic Ligand of the αvβ3 Vitronectin Receptor," *Bone* 23: S612 (1998); M. W. Lark et al., "An Orally Active Vitronectin Receptor αvβ3 Antagonist Prevents Bone Resorption In Vitro and In Vivo in the Ovariectomized Rat," *Bone* 23: S219 (1998)).

The αvβ3 integrin receptor recognizes the Arg-Gly-Asp (RGD) tripeptide sequence in its cognate matrix and cell surface glycoproteins (see J. Samanen, et al., "Vascular Indications for Integrin αv Antagonists," *Curr. Pharmaceut. Design* 3: 545–584 (1997)). A benzazepine nucleus has been employed among others by Genentech and SmithKline Beecham as a conformationally constrained Gly-Asp mimetic to elaborate nonpeptide αvβ3 integrin receptor antagonists substituted at the N-terminus with heterocyclic arginine mimetics (see R. M. Keenan et al., "Discovery of Potent Nonpeptide Vitronectin Receptor (αvβ3) Antagonists," *J. Med. Chem.* 40: 2289–2292 (1997); R. M. Keenan et al., "Benzimidazole Derivatives As Arginine Mimetics in 1,4-Benzodiazepine Nonpeptide Vitronectin Receptor (αvβ3) Antagonists," *Bioorg. Med. Chem. Lett.* 8: 3165–3170 (1998); and R. M. Keenan et al., "Discovery of an Imidazopyridine-Containing 1,4-Benzodiazepine Nonpeptide Vitronectin Receptor (αvβ3) Antagonist With Efficacy in a Restenosis Model," *Bioorg. Med. Chem. Lett.* 8: 3171–3176 (1998). Patents assigned to SmithKline Beecham that disclose such benzazepine, as well as related benzodiazepine and benzocycloheptene, αvβ3 integrin receptor antagonists include WO 96/00574, WO 96/00730, WO 96/06087, WO 96/26190, WO 97/24119, WO 97/24122, WO 97/24124, WO 98/14192, WO 98/15278, WO 99/05107, WO 99/06049, WO 99/15170, WO 99/15178, and WO 99/15506, and to Genentech include WO 97/34865. The dibenzocycloheptene, as well as dibenzoxazepine, nucleus has also been employed as a Gly-Asp mimetic to afford αvβ3 antagonists (see WO 97/01540, WO 98/30542, WO 99/11626, WO 99/15508, U.S. Pat. Nos. 6,008,213, and 6,069,158, all assigned to SmithKline Beecham).

Other integrin receptor antagonists incorporating backbone conformational ring constraints have been described in the patent literature. Published patent applications or issued patents disclosing antagonists having a phenyl constraint include WO 98/00395, WO 99/32457, WO 99/37621, WO 99/44994, WO 99/45927, WO 99/52872, WO 99/52879, WO 99/52896, WO 00/06169, EP 0 820,988, EP 0 820,991, U.S. Pat. Nos. 5,741,796; 5,773,644; 5,773,646; 5,843,906; 5,852,210; 5,929,120; 5,952,381; 6,028,223; and 6,040,311. Published patent applications or issued patents disclosing antagonists having a monocyclic ring constraint include WO 99/26945, WO 99/30709, WO 99/30713, WO 99/31099, WO 99/59992, WO 00/00486, WO 00/09503, EP 0 796,855, EP 0 928,790, EP 0 928,793, U.S. Pat. Nos. 5,710,159; 5,723,480; 5,981,546; 6,017,926; and 6,066,648. Published patent applications or issued patents disclosing antagonists having a bicyclic ring constraint include WO 98/23608, WO 98/35949, WO 99/33798, EP 0 853,084, U.S. Pat. Nos. 5,760,028; 5,919,792; and 5,925,655.

Reference is also made to the following reviews for additional scientific and patent literature that concern alpha v integrin antagonists: M. E. Duggan, et al., "Ligands to the integrin receptor αvβ3, *Exp. Opin. Ther. Patents*, 10: 1367–1383 (2000); M. Gowen, et al., "Emerging therapies for osteoporosis," *Emerging Drugs*, 5: 1–43 (2000); J. S. Kerr, et al., "Small molecule α$_v$ integrin antagonists: novel anticancer agents," *Exp. Opin. Invest. Drugs*, 9: 1271–1291 (2000); and W. H. Miller, et al., "Identification and in vivo efficacy of small-molecule antagonists of integrin α$_v$β3 (the vitronectin receptor)," *Drug Discovery Today*, 5: 397–408 (2000).

However, there still remains a need for small-molecule, non-peptidic selective αv integrin receptor antagonists that display improved potency, pharmacodynamic, and pharmacokinetic properties, such as oral bioavailability and duration of action, over already described compounds. Such compounds would provide an enhancement in the treatment, prevention, or suppression of various pathologies enumerated above that are mediated by αv integrin receptor binding and cell adhesion and activation.

In U.S. Pat. No. 6,017,926 (Jan. 25, 2000) and WO 99/31099 (published 24 Jun. 1999), we disclosed a series of imidazolidinone derivatives which are potent αvβ3 integrin receptor antagonists. In the present invention, we describe novel imidazolidinone derivatives which are substituted at the N-terminus with novel optionally substituted heterocycles and at C-3 with an optionally substituted aryl group. The compounds of the present invention exhibit improved in vivo pharmacokinetic and/or pharmacodynamic properties over the prior art compounds.

It is therefore an object of the present invention to provide novel imidazolidinone derivatives which are useful as αv integrin receptor antagonists.

It is another object of the present invention to provide novel imidazolidinone derivatives which are useful as αvβ3 receptor antagonists.

It is another object of the present invention to provide novel imidazolidinone derivatives which are useful as αvβ5 receptor antagonists.

It is another object of the present invention to provide novel imidazolidinone derivatives which are useful as dual αvβ3/αvβ5 receptor antagonists.

It is another object of the present invention to provide pharmaceutical compositions comprising αv integrin receptor antagonists.

It is another object of the present invention to provide methods for making the pharmaceutical compositions of the present invention.

It is another object of the present invention to provide methods for eliciting an αv integrin receptor antagonizing effect in a mammal in need thereof by administering the compounds and pharmaceutical compositions of the present invention.

It is another object of the present invention to provide compounds and pharmaceutical compositions useful for inhibiting bone resorption, restenosis, atherosclerosis, inflammatory arthritis, diabetic retinopathy, macular degeneration, angiogenesis, cancer, and metastatic tumor growth.

It is another object of the present invention to provide compounds and pharmaceutical compositions useful for treating osteoporosis.

It is another object of the present invention to provide methods for inhibiting bone resorption, restenosis, atherosclerosis, inflammatory arthritis, diabetic retinopathy, macular degeneration, angiogenesis, cancer, and metastatic tumor growth.

It is another object of the present invention to provide methods for treating osteoporosis.

These and other objects will become readily apparent from the detailed description which follows.

SUMMARY OF THE INVENTION

The present invention relates to novel imidazolidinone derivatives represented by structural formula (I), or a pharmaceutically acceptable salt thereof, which are useful as αv integrin receptor antagonists.

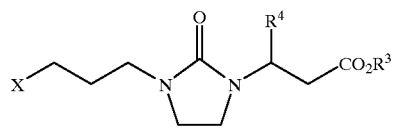

(I)

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an αv integrin receptor antagonizing effect in a mammal in need thereof by administering the compounds and pharmaceutical compositions of the present invention.

The present invention also relates to methods for inhibiting bone resorption, restenosis, atherosclerosis, inflammatory arthritis, diabetic retinopathy, macular degeneration, angiogenesis, cancer, and metastatic tumor growth by administering the compounds and pharmaceutical compositions of the present invention.

The present invention also relates to methods for treating osteoporosis by administering the compounds and pharmaceutical compositions of the present invention.

DETAILED DESCRIPTION OF THE INVENTION

The present invention relates to imidazolidinone derivatives useful as αv integrin receptor antagonists. Representative compounds of the present invention are described by the following structural formula (I):

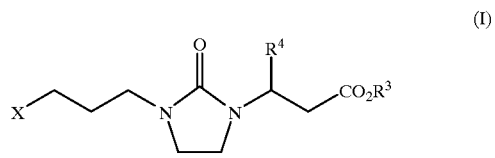

(I)

or a pharmaceutically acceptable salt thereof, wherein
X is selected from the group consisting of

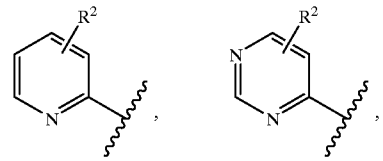

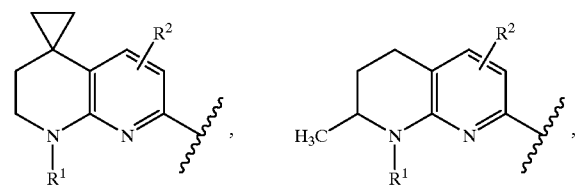

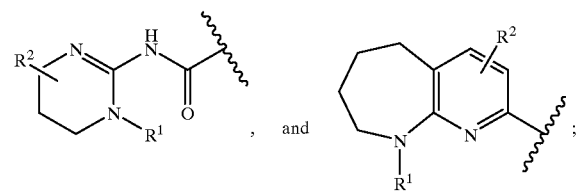

each $R^1$ is independently hydrogen or $C_{1-3}$ alkyl and each non-aromatic ring carbon atom is unsubstituted or independently substituted with one or two $R^2$ substituents and each aromatic ring carbon atom is unsubstituted or independently substituted with one $R^2$ substituent selected from the group consisting of $C_{1-8}$ alkyl, $C_{3-8}$ cycloalkyl, $C_{3-8}$ cycloheteroalkyl, $C_{3-8}$ cycloalkyl-$C_{1-6}$ alkyl, $C_{3-8}$ cycloheteroalkyl-$C_{1-6}$ alkyl, aryl, aryl-$C_{1-6}$ alkyl, amino-$C_{1-6}$ alkyl, $C_{1-3}$ acylamino, $C_{1-3}$ acylamino-$C_{1-6}$ alkyl, amino, $(C_{1-6}$ alkyl$)_{1-2}$ amino, $C_{3-6}$ cycloalkyl-$C_{0-2}$ amino, $(C_{1-6}$ alkyl$)_{1-2}$ amino-$C_{1-6}$ alkyl, $C_{1-6}$ alkoxy, $C_{1-4}$ alkoxy-$C_{1-6}$ alkyl, hydroxycarbonyl, hydroxycarbonyl-$C_{1-6}$ alkyl, $C_{1-3}$ alkoxycarbonyl, $C_{1-3}$ alkoxycarbonyl-$C_{1-6}$ alkyl, hydroxy, hydroxy-$C_{1-6}$ alkyl, nitro, cyano, trifluoromethyl, trifluoromethoxy, trifluoroethoxy, $C_{1-8}$ alkyl-$S(O)_{0-2}$, $(C_{1-8}$ alkyl$)_{0-2}$ aminocarbonyl, $C_{1-8}$ alkyloxycarbonylamino, $(C_{1-8}$ alkyl$)_{1-2}$ aminocarbonyloxy, (aryl)$_{1-2}$ amino, aryl-$C_{1-3}$ alkylsulfonylamino, and $C_{1-8}$ alkylsulfonylamino;

or two $R^2$ substituents, when on the same non-aromatic carbon atom, are taken together with the carbon atom to which they are attached to form a carbonyl group;

or two $R^2$ substituents, together with the carbon atom to which they are attached, join to form a 3- to 6-membered saturated spiro-carbocyclic ring;

R[4] is aryl wherein the aryl group is selected from the group consisting of
(1) phenyl,
(2) naphthyl,
(3) pyridyl,
(4) furyl,
(5) thienyl,
(6) pyrrolyl,
(7) oxazolyl,
(8) thiazolyl,
(9) imidazolyl,
(10) pyrazolyl,
(11) isoxazolyl,
(12) isothiazolyl,
(13) pyrimidinyl,
(14) pyrazinyl,
(15) pyridazinyl,
(16) quinolyl,
(17) isoquinolyl,
(18) benzimidazolyl,
(19) benzofuryl,
(20) benzothienyl,
(21) indolyl,
(22) benzthiazolyl,
(23) benzoxazolyl,
(24) dihydrobenzofuryl,
(25) benzo(1,3)dioxolanyl, and
(26) benzo(1,4)dioxanyl;
and mono, di, and tri-substituted aryl wherein the substituents are independently hydrogen, hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino-$C_{1-6}$ alkyl, di($C_{1-6}$)alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_1 16$ alkyl, hydroxycarbonyl, hydroxycarbonyl-$C_{16}$ alkyl, $C_{1-5}$ alkoxycarbonyl, $C_{1-3}$ alkoxycarbonyl-$C_{1-6}$ alkyl, $C_{1-5}$ alkylcarbonyloxy, cyano, trifluoromethyl, 1,1,1-trifluoroethyl, trifluoromethoxy, trifluoroethoxy, or nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl; and R[3] is hydrogen or $C_{1-3}$ alkyl.

In one embodiment of the present invention, X is selected from the group consisting of:

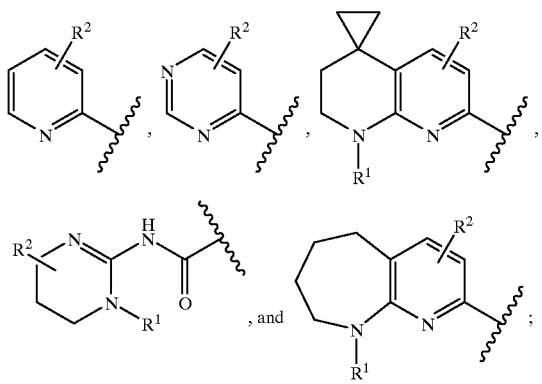

In a second embodiment of the present invention, R[4] is mono- or di-substituted phenyl,
pyridyl,
quinolyl,
pyrimidinyl,
pyrazinyl,
pyrazolyl, or
dihydrobenzofuryl;
wherein the substituents are independently hydrogen, hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino-$C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino $C_{1-6}$ alkyl, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl $C_{1-6}$ alkyl, $C_{1-5}$ alkylcarbonyloxy, cyano, trifluoromethyl, 1,1,1-trifluoroethyl, trifluoromethoxy, trifluoroethoxy, or nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl.

In a class of this second embodiment of the present invention, R[4] is mono- or di-substituted
quinolyl,
pyridyl, or
pyrimidinyl;
wherein the substituents are independently hydrogen, halogen, phenyl, $C_{1-4}$ alkyl, $C_{3-6}$ cycloalkyl, $C_{1-3}$ alkoxy, amino, $C_{1-3}$ alkylamino, di($C_{1-3}$) alkylamino, hydroxy, cyano, trifluoromethyl, 1,1,1-trifluoroethyl, trifluoromethoxy, or trifluoroethoxy.

In a third embodiment of the present invention, R[2] is selected from the group consisting of
hydrogen,
$C_{1-4}$ alkylamino,
$C_{3-6}$ cycloalkyl-$C_{0-2}$ alkylamino
cyano,
$C_{1-4}$ alkyl,
cyclopropyl,
aryl $C_{1-3}$ alkyl,
$C_{1-4}$ acylamino,
$C_{1-4}$ alkoxy,
$C_{1-4}$ alkylthio,
aminocarbonyl,
($C_{1-6}$ alkyl)$_{1-2}$ aminocarbonyl,
$C_{1-4}$ alkoxycarbonyl,
trifluoromethyl, and
trifluoromethoxy.

In a class of this third embodiment of the present invention, R[2] is selected from the group consisting of
hydrogen,
$C_{1-3}$ alkylamino,
$C_{3-6}$ cycloalkylmethylamino,
$C_{1-4}$ alkyl,
cyclopropyl,
trifluoromethyl, and
trifluoromethoxy.

Illustrative but nonlimiting examples of compounds of the present invention that are useful as αv integrin receptor antagonists are the following:

3-(6-methoxy-pyridin-3-yl)-3-{2-oxo-3-[3-(1,4,5,6-tetrahydro-pyrimidin-2-ylcarbamoyl)-propyl]-imidazolidin-1-yl}-propionic acid;

3(R)-(6-methoxy-pyridin-3-yl)-3-{2-oxo-3-[3-(1,4,5,6-tetrahydro-pyrimidin-2-ylcarbamoyl)-propyl]-imidazolidin-1-yl}-propionic acid;

3 (S)-(6-methoxy-pyridin-3-yl)-3-{2-oxo-3-[3-(1,4,5,6-tetrahydro-pyrimidin-2-ylcarbamoyl)-propyl]-imidazolidin-1-yl}-propionic acid;

3-(3-{3-[6-(Cyclopropylmethyl-amino)-pyridin-2-yl]-propyl}-2-oxo-imidazolidin-1-yl)-3-(6-methoxy-pyridin-3-yl)-propionic acid;

3-(3-{3-[6-(Cyclopropylmethyl-amino)-pyridin-2-yl]-propyl}-2-oxo-imidazolidin-1-yl)-3(R)-(6-methoxy-pyridin-3-yl)-propionic acid;

3-(3-{3-[6-(Cyclopropylmethyl-amino)-pyridin-2-yl]-propyl}-2-oxo-imidazolidin-1-yl)-3(S)-(6-methoxy-pyridin-3-yl)-propionic acid;

3-(6-Methoxy-pyriidin-3-yl)-3-1 2-oxo-3-[3-(6,7,8,9-tetrahydro-5H-pyrido[2,3-b]azepin-2-yl)-propyl]-imidazolidin-1-yl}-propionic acid;

3(R)-(6-Methoxy-pyridin-3-yl)-3-{2-oxo-3-[3-(6,7,8,9-tetrahydro-5H-pyrido[2,3-b]azepin-2-yl)-propyl]-imidazolidin-1-yl }-propionic acid;

3(S)-(6-Methoxy-pyridin-3-yl)-3-{2-oxo-3-[3-(6,7,8,9-tetrahydro-5H-pyrido[2,3-b]azepin-2-yl)-propyl]-imidazolidin-1-yl }-propionic acid;

3-(6-Ethoxypyridin-3-yl)-3-{2-oxo-3-[3-(1,4,5,6-tetrahydro-pyrimidin-2-ylcarbamoyl)-propyl]-imidazolidin-1-yl}-propionic acid;

3(R)-(6-Ethoxypyridin-3-yl)-3-{2-oxo-3-[3-(1,4,5,6-tetrahydro-pyrimidin-2-ylcarbamoyl)-propyl]-imidazolidin-1-yl}-propionic acid;

3(S)-(6-Ethoxypyridin-3-yl)-3-{2-oxo-3-[3-(1,4,5,6-tetrahydro-pyrimidin-2-ylcarbamoyl)-propyl]-imidazolidin-1-yl }-propionic acid;

3-(6-Ethoxy-pyridin-3-yl)-3-{2-oxo-3-[3-(4-methyl-1,4,5,6-tetrahydropyrimidin-2-ylcarbamoyl)-propyl] imidazolidin-1-yl]-propionic acid;

3(R)-(6-Ethoxy-pyridin-3-yl)-3-{2-oxo-3-[3-(4-methyl-1,4,5,6-tetrahydropyrimidin-2-ylcarbamoyl)-propyl]-imidazolidin-1-yl}-propionic acid;

3(S)-(6-Ethoxy-pyridin-3-yl)-3-{2-oxo-3-[3-(4-methyl-1,4,5,6-tetrahydropyrimidin-2-ylcarbamoyl)-propyl]-imidazolidin-1-yl}-propionic acid;

3-(dihydrobenzofuran-6-yl)-3-{2-oxo-3-[3-(1,4,5,6-tetrahydro-pyrimidin-2-ylcarbamoyl)-propyl]-imidazolidin-1-yl}-propionic acid;

3(R)-(dihydrobenzofuran-6-yl)-3-{2-oxo-3-[3-(1,4,5,6-tetrahydro-pyrimidin-2-ylcarbamoyl)-propyl]-imidazolidin-1-yl}-propionic acid;

3(S)-(dihydrobenzofuran-6-yl)-3-{2-oxo-3-[3-(1,4,5,6-tetrahydro-pyrimidin-2-ylcarbamoyl)-propyl]-imidazolidin-1-yl}-propionic acid;

3-(dihydrobenzofuran-6-yl)-3-{2-oxo-3-[3-(4-amino-2-ethylaminopyriidin-6-yl)-propyl]-imidazolidin-1-yl}-propionic acid;

3(R)-(dihydrobenzofuran-6-yl)-3-{2-oxo-3-[3-(4-amino-2-ethylaminopyriidin-6-yl)-propyl]-imidazolidin-1-yl}-propionic acid;

3(S)-(dihydrobenzofuran-6-yl)-3-{2-oxo-3-[$^3$-($^4$-amino-2-ethylaminopyrimidin-6-yl)-propyl]-imidazolidin-1-yl}-propionic acid;

3-(6-methoxy-pyridin-3-yl)-3-{2-oxo-3-(5,6,7,8-tetrahydro-5,5-ethyleno-[1,8]naphthyridin-2-yl)-propyl]-imidazolidin-1-yl-propionic acid;

3(R)-(6-methoxy-pyridin-3-yl)-3-{2-oxo-3-(5,6,7,8-tetrahydro-5,5-ethyleno-[1,8]naphthyridin-2-yl)-propyl]-imidazolidin-1-yl-propionic acid;

3(S)-(6-methoxy-pyridin-3-yl)-3-{2-oxo-3-(5,6,7,8-tetrahydro-5,5-ethyleno-[1,8]naphthyridin-2-yl)-propyl]-imidazolidin-1-yl-propionic acid; and 3(S)-(6-Methoxy-pyridin-3-yl)-3-2-oxo-3-(7-methyl-5,6,7,8-tetrahydro-[1,8]naphthyridin-2-yl)-propyl]-imidazolidin-1-yl}-propionic acid;

or a pharmaceutically acceptable salt thereof.

In certain embodiments of the present invention, the compounds correspond to the formula (II) with the designated stereochemistry at the carbon atom where $R^4$ is attached:

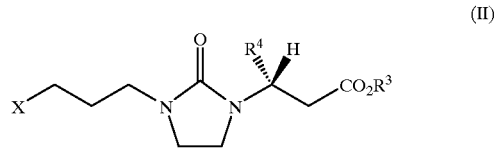

(II)

wherein the substituents X, $R^1$, $R^2$, $R^3$, and $R^4$ are as described above.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts of basic compounds encompassed within the term "pharmaceutically acceptable salts" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compounds of the present invention can have chiral centers and can thus occur as racemates, racemic mixtures, single enantiomers, diastereomeric mixtures, and individual diastereomers, with all isomeric forms being included in the present invention. Therefore, where a compound is chiral, the separate enantiomers or diastereomers, substantially free of the other, are included within the scope of the invention; further included are all mixtures of the two enantiomers.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form, known as keto-enol tautomers. The individual tautomers as well as mixtures thereof are encompassed within the compounds of the present invention.

Compounds of the present invention may be separated into diastereoisomeric pairs of enantiomers by, for example, fractional crystallization from a suitable solvent, for example, methanol or ethyl acetate or a mixture thereof. The pair of enantiomers thus obtained may be separated into individual stereoisomers by conventional means, for example, by the use of an optically active acid as a resolving agent, or by BPLC using a chiral stationary phase. Alternatively, any enantiomer of a compound of the present invention may be obtained by stereospecific synthesis using optically pure starting materials or reagents of known configuration.

Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "αv integrin receptor antagonist," as used herein, refers to a compound which binds to and antagonizes either the αvβ3 receptor or the αvβ5 receptor, or a compound which binds to and antagonizes a combination of these receptors (for example, a dual αvβ3/αvβ5 receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O, or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or bicyclic system comprising at least one aromatic ring, wherein the monocylic or bicyclic system contains 0, 1, 2, 3, or 4 heteroatoms chosen from N, O, or S, and wherein the monocylic or bicylic system is either unsubstituted or substituted with one or more groups independently selected from hydrogen, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylamino, $C_{1-6}$ alkylamino $C_{1-6}$ alkyl, di($C_{1-6}$) alkylamino, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, trifluoromethoxy, oxo, or $C_{1-5}$ alkylcarbonyloxy. Examples of aryl include, but are not limited to, phenyl, naphthyl, pyridyl, pyrrolyl, pyrazolyl, pyrazinyl, pyrimidinyl, imidazolyl, benzimidazolyl, benzthiazolyl, benzoxazolyl, indolyl, thienyl, furyl, dihydrobenzofuryl, benzo(1,3) dioxolanyl, benzo(1,4)dioxanyl, oxazolyl, isoxazolyl, thiazolyl, and isothiazolyl, which are either unsubstituted or substituted with one or more groups independently selected from hydrogen, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino $C_{1-6}$ alkyl, $C_{1-6}$ alkylamino, $C_{1-6}$ alkylamino $C_{1-6}$ alkyl, di($C_{1-6}$) alkylamino, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, trifluoromethoxy, oxo, or $C_{1-5}$ alkylcarbonyloxy. Preferably, the aryl group is unsubstituted, mono-, di-, or tri- substituted with one to three of the above-named substituents; more preferably, the aryl group is unsubstituted, mono- or di-substituted with one to two of the above-named substituents.

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{1-8}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

In the compounds of the present invention, two $R^2$ substituents, when on the same carbon atom, can be taken together with the carbon atom to which they are attached to form a carbonyl group.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

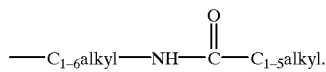

In choosing compounds of the present invention, one of ordinary skill in the art will recognize that the various substituents, i.e. X, $R^1$, $R^2$, $R^3$, and $R^4$ are to be chosen in conformity with well-known principles of chemical structure connectivity.

Representative compounds of the present invention typically display submicromolar affinity for the αv integrin receptors, particularly the αvβ3 and/or αvβ5 receptors. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis.

Illustrating the invention is the method wherein the αv integrin receptor antagonizing effect is an αvβ3 antagonizing effect. More particularly, the αvβ3 antagonizing effect is selected from inhibition of: bone resorption, restenosis, angiogenesis, diabetic retinopathy, macular degeneration, inflammation, inflammatory arthritis, viral disease, cancer, or metastatic tumor growth. In one embodiment of the method, the αvβ3 antagonizing effect is the inhibition of bone resorption.

Another example of the invention is the method wherein the αv integrin receptor antagonizing effect is an αvβ5 antagonizing effect. More specifically, the αvβ5 antagonizing effect is selected from inhibition of restenosis, angiogenesis, diabetic retinopathy, macular degeneration, inflammation, cancer, or metastatic tumor growth.

Further illustrating the invention is the method wherein the αv integrin receptor antagonizing effect is a dual αvβ3/αvβ5 antagonizing effect. More particularly, the dual αvβ3/αvβ5 antagonizing effect is selected from inhibition of: bone resorption, restenosis, angiogenesis, diabetic retinopathy, macular degeneration, inflammation, viral disease, cancer, or metastatic tumor growth.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of an αv integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammation, inflammatory arthritis, viral disease, cancer, tumor growth, and metastasis. More preferably, the condition is selected from osteoporosis and cancer. Most preferably, the condition is osteoporosis.

More specifically exemplifying the invention is a method of eliciting an αv integrin antagonizing effect in a mammal in need thereof, comprising administering to the mammal a therapeutically effective amount of any of the compounds or any of the pharmaceutical compositions described above. Preferably, the αv integrin antagonizing effect is an αvβ3 antagonizing effect; more specifically, the αvβ3 antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation, or inhibition of cancer or metastatic tumor growth. Most preferably, the αvβ3 antagonizing effect is inhibition of bone resorption. Alternatively, the integrin antagonizing effect is an αvβ5 antagonizing effect or a dual αvβ3/αvβ5 antagonizing effect. Examples of αvβ5 antagonizing effects are inhibition of restenosis, atherosclerosis, angiogenesis, diabetic retinopathy, macular degeneration, inflammation, cancer, or metastatic tumor growth.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions described above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone resorption, cancer, metastatic tumor growth, restenosis, atherosclerosis, diabetic retinopathy, macular degeneration, inflammatory arthritis, and/or angiogenesis.

Also exemplifying the invention are compositions further comprising an active ingredient selected from the group consisting of
- a) an organic bisphosphonate or a pharmaceutically acceptable salt or ester thereof,
- b) an estrogen receptor modulator,
- c) an androgen receptor modulator,
- d) a cytotoxic/antiproliferative agent,
- e) a matrix metalloproteinase inhibitor,
- f) an inhibitor of epidermal-derived, fibroblast-derived, or platelet-derived growth factors,
- g) an inhibitor of VEGF,
- h) an antibody to a growth factor or to a growth factor receptor,
- i) an inhibitor of Flk-1/KDR, Flt-1, Tck/Tie-2, or Tie-1,
- j) a cathepsin K inhibitor,
- k a growth hormone secretagogue,
- l) an inhibitor of osteoclast proton ATPase,
- m) an inhibitor of urokinase plasminogen activator (u-PA),
- n) a tumor-specific antibody-interleukin-2 fusion protein,
- o) an inhibitor of HMG-CoA reductase,
- p) a prenylation inhibitor, such as a farnesyl transferase inhibitor or a geranylgeranyl transferase inhibitor or a dual farnesyl/geranylgeranyl transferase inhibitor; and
- q) human parathyroid hormone (hPTH) or human parathyroid hormone fragment (1-34);

and mixtures thereof.
(See, B. Millauer et al., "Dominant-Negative Inhibition of Flk-1 Suppresses the Growth of Many Tumor Types in Vivo", *Cancer Research,* 56, 1615–1620 (1996), which is incorporated by reference herein in its entirety).

Preferably, the active ingredient is selected from the group consisting of:
- a) an organic bisphosphonate or a pharmaceutically acceptable salt or ester thereof,
- b) an estrogen receptor modulator,
- c) an androgen receptor modulator,
- d) an inhibitor of osteoclast proton ATPase,
- e) an inhibitor of HMG-CoA reductase, and
- f) a cathepsin K inhibitor; and mixtures thereof.

Nonlimiting examples of such bisphosphonates include alendronate, cimadronate, clodronate, etidronate, ibandronate, pamidronate, pimidronate, risedronate, tiludronate, and zolendronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

Members of the class of HMG-CoA reductase inhibitors, known as the "statins," have been found to trigger the growth of new bone, replacing bone mass lost as a result of osteoporosis (see *The Wall Street Journal,* Friday, Dec. 3, 1999, page B1). Therefore, the statins hold promise for the treatment of bone resorption. Nonlimiting examples of statins are lovastatin, simvastatin, atorvastatin, pravastatin, fluvastatin, cerivastatin, and rosuvastatin. Evidence for crucial role of the urokinase-urokinase receptor (u-PA-u-PAR) in angiogenesis, tumor invasion, inflammation, and matrix remodeling during wound healing and development has been presented [see Y. Koshelnick et al., "Mechanisms of signaling through Urokinase Receptor and the Cellular Response," *Thrombosis and Haemostasis* 82: 305–311 (1999) and F. Blasi, "Proteolysis, Cell Adhesion, Chemotaxis, and Invasiveness Are Regulated by the u-PA-u-PAR-PAI-1 System," *Thrombosis and Haemostasis* 82: 298–304 (1999)]. Thus, specific antagonists of the binding of u-PA to u-PAR have been found to inhibit cell-surface plasminogen activation, tumor growth, and angiogenesis in both in vitro and in vivo models.

H. N. Lode and coworkers in *PNAS USA* 96: 1591–1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth.

The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases (see C. Farina et al., "Selective inhibitors of the osteoclast vacuolar proton ATPase as novel bone antiresorptive agents," *DDT,* 4:163–172 (1999)).

Evidence has been presented that androgenic steroids play a physiological role in the development of bone mass in men and women and that androgens act directly on bone. Androgen receptors have been demonstrated in human osteoblast-like cell lines and androgens have been shown to directly stimulate bone cell proliferation and differentiation. For a discussion, reference is made to S. R. Davis, "The therapeutic use of androgens in women," *J. Steroid Biochem. Mol. Biol.,* 69: 177–184 (1999) and K. A. Hansen and S. P. T. Tho, "Androgens and Bone Health," *Seminars in Reproductive Endocrinology,"* 16: 129–134 (1998). Thus, androgen receptor modulators may have utility in the treatment and prevention of bone loss in women.

The angiogenic factor VEGF has been shown to stimulate the bone-resorbing activity of isolated mature rabbit osteoclasts via binding to its receptors on osteoclasts (see M. Nakagawa et al., "Vascular endothelial growth factor (VEGF) directly enhances osteoclastic bone resorption and survival of mature osteoclasts," *FEBS Letters*, 473: 161–164 (2000)). Therefore, the development of antagonists of VEGF binding to osteoclast receptors, such as KDR/Flk-1 and Flt-1, may provide yet a further approach to the treatment or prevention of bone resorption.

Activators of the peroxisome proliferator-activated receptor-γ(PPARγ), such as the thiazolidinediones (TZD's), inhibit osteoclast-like cell formation and bone resorption in vitro. Results reported by R. Okazaki et al. in *Endocrinology*, 140: 5060–5065 (1999) point to a local mechanism on bone marrow cells as well as a systemic one on glucose metabolism. Nonlimiting examples of PPARγ activators include troglitazone, pioglitazone, rosiglitazone, and BRL 49653.

Parathyroid hormone (PTH) is the major circulating hormone, secreted by the parathyroid gland, that functions to maintain calcium homeostasis. PTH has been shown to increase the activity of osteoblasts, the cells that form bone, and to increase bone size as well as density. The PTH fragment hPTH(1-34) has been demonstrated to have anabolic effects in osteoporotic humans. A large clinical trial of the effect of hPTH(1-34) on postmenopausal osteoporotic women reported $\geq 65\%$ reduction in spine fractures and a 54% reduction in nonvertebral fractures after a median of 22 months of treatment (see J. M. Hock, ""Discrimination among osteoblasts? Parathyroid Hormone Analog May Reveal Site-Specific Differences in Mice," Bone, 27: 467–469 (2000) and references cited therein). Hence, PTH and fragments thereof, such as hPTH(1-34) (LY333334), are other potential agents for the treatment of osteoporosis.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, an androgen receptor modulator, a cathepsin K inhibitor, an HMG-CoA reductase inhibitor, a PPARγ activator, or an inhibitor of the osteoclast proton ATPase.

Additional illustrations of the invention are methods of treating tumor growth or metastasis in a mammal in need thereof, comprising administering to the mammal a therapeutically effective amount of a compound described above and one or more agents known to be cytotoxic/antiproliferative. Also, the compounds of the present invention can be administered in combination with radiation therapy for treating cancer and metastatic tumor growth.

In addition, the integrin αvβ3 antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid-induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the Schemes and Examples below, various reagent symbols and abbreviations have the following meanings:

| | |
|---|---|
| AcOH: | Acetic acid. |
| BH$_3$.DMS: | Borane.dimethylsulfide. |
| BOC(Boc): | t-Butyloxycarbonyl. |
| BOP: | Benzotriazol-1-yloxytris(dimethylamino)-phosphonium hexafluorophosphate. |
| CBZ(Cbz): | Carbobenzyloxy or benzyloxycarbonyl. |
| CDI: | Carbonyldiimidazole. |
| CH$_2$Cl$_2$: | Methylene chloride. |
| CH$_3$CN: | Acetonitrile |
| CHCl$_3$: | Chloroform. |
| DEAD: | Diethyl azodicarboxylate. |
| DIAD: | Diisopropyl azodicarboxylate. |
| DIBAH or DIBAL-H: | Diisobutylaluminum hydride. |
| DIPEA: | Diisopropylethylamine. |
| DMAP: | 4-Dimethylaminopyridine. |
| DME: | 1,2-Dimethoxyethane. |
| DMF: | N,N-Dimethylformamide. |
| DMSO: | Dimethylsulfoxide. |
| DPPF: | 1,1'-Bis(diphenylphosphino)-ferrocene. |
| DPFN: | 3,5-Dimethyl-1-pyrazolylformamidine nitrate. |
| EDC: | 1-(3-Dimethylaminopropyl)-3-ethylcarbodiimide.HCl |
| EtOAc: | Ethyl acetate. |
| EtOH: | Ethanol. |
| HOAc: | Acetic acid. |
| HOAT: | 1-Hydroxy-7-azabenzotriazole |
| HOBT: | 1-Hydroxybenzotriazole. |
| HPLC: | High-performance liquid chromatography |
| IBCF: | Isobutylchloroformate |
| LDA: | Lithium diisopropylamide. |
| MeOH: | Methanol. |
| MNNG: | 1,1-methyl-3-nitro-1-nitrosoguanidine. |
| MTBE | Methyl tert-butyl ether |
| NEt$_3$: | Triethylamine. |
| NMM: | N-methylmorpholine. |
| PCA.HCl: | Pyrazole carboxamidine hydrochloride. |
| Pd/C: | Palladium on activated carbon catalyst. |
| Ph: | Phenyl. |
| PyCLU: | Chloro-N,N,N',N'-(tetramethylene)-formamidinium hexafluorophosphate. |
| TBTU | O-Benzotriazol-1-yl-N,N,N',N'-tetramethyluronium tetrafluoroborate. |
| pTSA | p-Toluenesulfonic acid. |
| TEA: | Triethylamine. |
| TFA: | Trifluoroacetic acid. |
| THF: | Tetrahydrofuran. |
| TLC: | Thin Layer Chromatography. |
| TMEDA: | N,N,N',N'-Tetramethylethylenediamine. |
| TMS: | Trimethylsilyl. |

The novel compounds of the present invention can be prepared according to the procedures of the following reaction Schemes and Examples, or modifications thereof, using readily available starting materials, reagents, and, where appropriate, conventional synthetic procedures. In these procedures, it is also possible to make use of variants which are themselves known to those of ordinary skill in the organic synthetic arts, but are not mentioned in greater detail.

The following Examples are illustrative of the more preferred compounds of the present invention. They are not, however, to be construed as forming the only genus that is considered as the invention. The Examples further illustrate details for preparation of the compounds of the present invention. Those skilled in the art will readily understand that known variations of the conditions and processes of the following preparative procedures can be used to prepare these compounds. Unless stated otherwise, all operations were carried out at room or ambient temperature, and all temperatures are degrees Celsius.

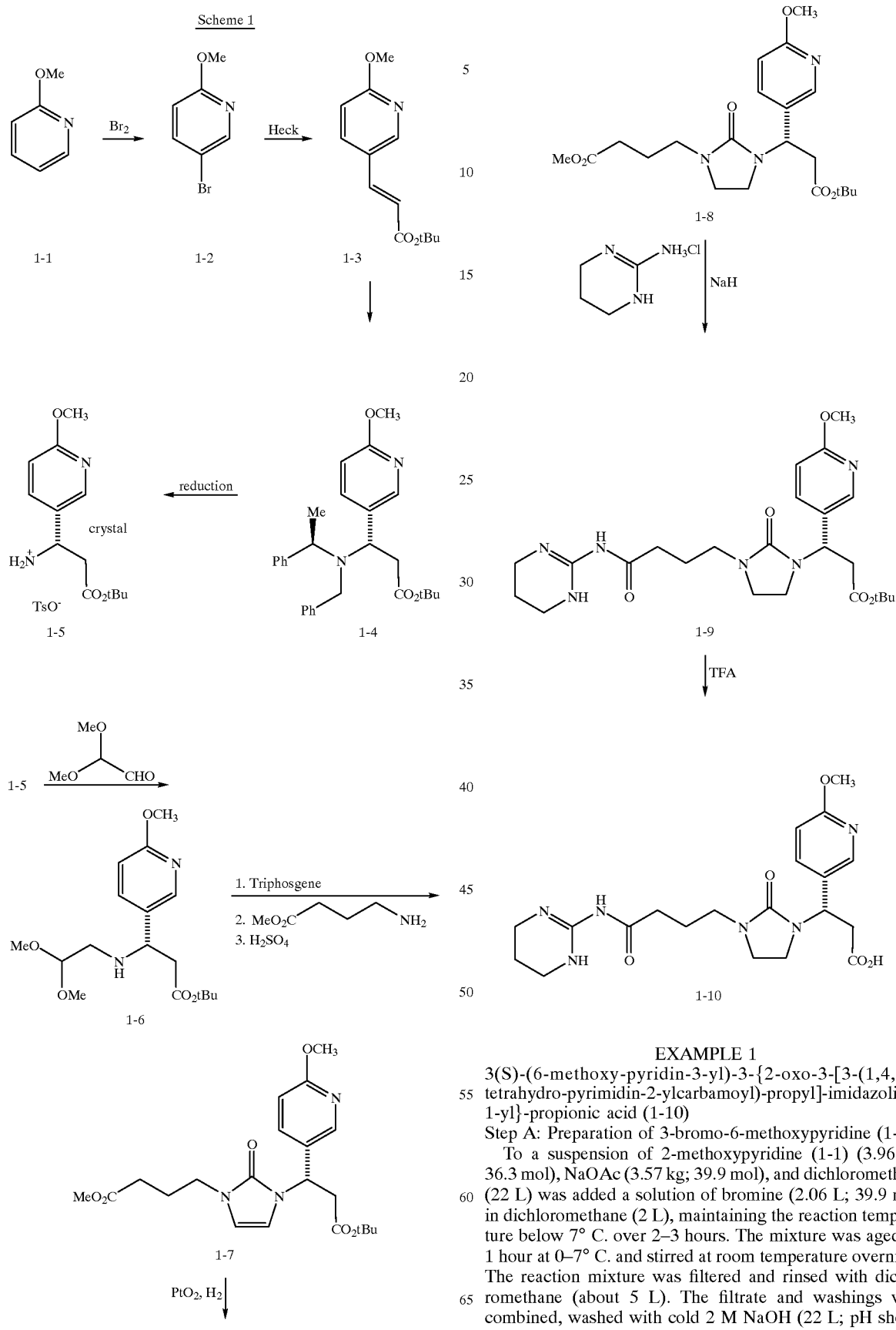

EXAMPLE 1

3(S)-(6-methoxy-pyridin-3-yl)-3-{2-oxo-3-[3-(1,4,5,6-tetrahydro-pyrimidin-2-ylcarbamoyl)-propyl]-imidazolidin-1-yl}-propionic acid (1-10)

Step A: Preparation of 3-bromo-6-methoxypyridine (1-2)

To a suspension of 2-methoxypyridine (1-1) (3.96 kg; 36.3 mol), NaOAc (3.57 kg; 39.9 mol), and dichloromethane (22 L) was added a solution of bromine (2.06 L; 39.9 mol) in dichloromethane (2 L), maintaining the reaction temperature below 7° C. over 2–3 hours. The mixture was aged for 1 hour at 0–7° C. and stirred at room temperature overnight. The reaction mixture was filtered and rinsed with dichloromethane (about 5 L). The filtrate and washings were combined, washed with cold 2 M NaOH (22 L; pH should be below 8) maintaining the temperature below 10° C., and with cold water (11 L). The organic layer was separated and concentrated under reduced pressure to give a crude product 1-2 (6.65 kg). The crude product was purified by vacuum distillation to give pure 1-2 (5.90 kg, 86%). Known compound: G. Butora et al., JACS, 119, 7694–7701 (1997).
$^1$H NMR (250 MHz; CDCl$_3$): δ 8.18 (d, J=2.5 Hz, 1H), 7.61 (dd, J=8.8 and 2.5 Hz, 1H), 6.64 (d, J=8.8 Hz, 1H), and 3.89 (s, 3H).
$^{13}$C NMR (62.9 MHz, CDCl$_3$): δ 162.9, 147.5, 141.0, 112.6, 111.7, and 53.7.

Step B: Preparation of tert-butyl 3-(6-methoxypyridin-3-yl) acrylate (1-3)

A mixture of tert-butyl acrylate (98%; 137 mL; 916 mmol), triethylamine (100 mL; 720 mmol), tri-O-tolylphosphine (97%; 6.30 g; 20 mmol), Pd(OAc)$_2$ (1.80 g; 8 mmol), and NMP (90 mL) was degassed three times. The mixture was heated to 90° C., and a solution of 2-methoxy-5-bromopyridine 1-2(50.0 g; 266 mmol) and NMP (10 mL) was added via addition funnel over 1 hour, maintaining the reaction temperature at 90° C. The reaction was heated for 12 hours after complete addition. The reaction mixture was cooled down to room temperature after completion of the reaction. To the reaction mixture was added toluene (400 mL), and the resulting solution was then passed through a pad of Solka Flok. The filter cake was washed with toluene (270 mL). The toluene solution was washed with water (3×540 mL). An aqueous solution of sodium hypochlorite (NaClO) (2.5%; 200 mL) was slowly added to the toluene solution keeping the temperature about 30° C. The reaction was aged 50 min with a vigorous stirring. The organic layer was separated, washed with water (540 mL) three times, and followed by saturated aqueous NaCl (270 mL). The organic layer was concentrated to oil. The oil was dissolved in 270 mL hexanes and loaded onto to a silica gel (90 g) pad. The silica gel pad was washed with hexanes (73 mL). The product 1-3was eluted with EtOAc:hexane (1:8; v/v) in about 730 mL. The yellow solution was concentrated to oil (126 g; 49.2 wt %; 98.4% yield). The crude oil was used for the next reaction without further purification. Authentic sample was obtained by further concentration of the oil.
$^1$H NMR (250 MHz; CDCl$_3$): δ 8.23 (d, J=2.4 Hz, 1H), 7.73 (dd, J=8.7 and 2.4 Hz, 1H), 7.50 (d, J=16.0 Hz, 1H), 6.73 (d, J=8.7 Hz, 1H), 6.25 (d, J=16.0 Hz, 1H), 3.94 (s, 3H), and 1.51 (s, 9H).
$^{13}$C NMR (62.9 MHz; CDCl$_3$): δ 166.1, 165.1, 148.1, 139.9, 136.3,124.0, 119.1, 111.5, 80.6, 53.7, and 28.2.

Step C: Preparation of tert-butyl 3(S)-( (R)-N-benzyl-α-methylbenzylamine)-3-(6-methoxypyridin-3-yl)propionate (1-4)

To a solution of R-(+)-N-benzyl-α-methylbenzylamine (88 mL; 0.42 mol) and anhydrous TBF (1 L) was added n-BuLi (2.5M in hexanes; 162 mL; 0.41 mol) over 1 hour at −30° C. The solution was then cooled to −65° C. A solution of t-butyl ester 1-3(65.9 g; 0.28 mol) in anhydrous THF (0.5 L) was added over 90 minutes during which the temperature rose to −57° C. After the reaction was complete, the reaction solution was poured into a mixture of saturated aqueous NH$_4$Cl (110 mL) and EtOAc (110 mL). The organic layer was separated, washed separately with aqueous AcOH (10%; 110 mL), water (110 mL) and saturated aqueous NaCl (55 mL). The organic layer was concentrated in vacuo to a crude oil. The crude oil was purified by passing through a silica gel (280 g) pad with a mixture of EtOAc and hexanes (5:95). The fractions containing the product were combined and concentrated in vacuo to give a thick oil. The resulting oil was used directly in the next step. The oil contained 91 g (0.20 mol, 73% yield) of the product 1-4.

$^1$H NMR (250 MHz; CDCl$_3$): δ 8.15 (d, J=2.4 Hz, 1H), 7.65 (dd, J=8.6 and 2.4 Hz, 1H), 7.42-7.15 (m, 10H), 6.73 (d, J=8.6 Hz, 1H), 4.38 (dd, J=9.4 and 5.6 Hz, 1H), 3.96 (q, J=7.0 Hz, 2H), 3.93 (s, 3H), 3.66 (s, 2H), 2.50 (m, 2H), 1.28 (d, J=7.0 Hz, 3H), and 1.26 (s, 9 H).
$^{13}$C NMR (62.9 MHz: CDCl$_3$): δ 170.8, 163.3, 146.4, 143.8, 141.3, 138.6, 130.0, 128.3, 128.2, 127.9, 127.8, 127.0, 126.7, 110.4, 80.5, 57.4, 56.6, 53.4, 50.7, 37.5, 27.8, and 17.3.

Step D: Preparation of tert-butyl 3(S)-amino-3-(6-methoxypyridin-3-yl)propionate tosylate (1-5)

The thick oil (1–4; containing 80.3 g; 0.18 mol) was hydrogenated in the presence of Pd(OH)$_2$ (20 wt % on carbon; 8.0 g) in a mixture of EtOH (400 mL), AcOH (40 mL), water (2 mL) under 40 psi of hydrogen at 35° C. for 8 hours. The reaction mixture was filtered through a pad of Solka Flok, evaporated to a thick oil in vacuo, and flushed with MTBE (2 L each) several times. Upon cooling, the batch solidified to a thick white solid. The thick slurry was heated to 50° C. and the solids dissolved. A hot solution (40° C.) of p-toluenesulfonic acid (p-TsOH; 41.7 g; 0.22 mol) and MTBE (400 mL) was then transferred slowly to the warm solution of the amine. After ~30% of the p-TsOH solution had been added, the solution was seeded and a thick slurry formed. The addition was continued and was complete in 2 hours. The solution was aged after completion of the addition for 3 hours at 45° C. The solution was then slowly cooled to room temperature. The solution was aged for 12 hours at room temperature and then cooled to 6° C. The very thick slurry was filtered, washed with MTBE (100 mL) and dried under vacuum at 35° C. for several days to give the product 1-5(71.0 g; 73%).
mp: 142–144° C.
$^1$H NMR (250 MHz; CDCl$_3$): δ 8.32 (bs, 3 H), 8.12 (d, J=2.3 Hz, 1H), 7.77 (dd, J=8.7 and 2.3 Hz, 1H), 7.52 (d, J=8.1 Hz, 2H), 7.07 (d, J=8.1 Hz, 2H), 6.56 (d, J=8.7 Hz, 1H), 4.56 (m, 1H), 3.87 (s, 3H), 3.03 (dd, J=16.3 and 5.7 Hz, 1H), 2.81 (dd, J=16.3 and 9.2 Hz, 1H), 2.35 (s, 3H), and 1.23 (s, 9H).
$^{13}$C NMR (62.9 MHz; CDCl$_3$): δ 168.4, 163.9, 146.4, 141.0, 140.4, 138.5, 128.8, 125.8, 124.5, 110.9, 81.6, 53.7, 49.5, 39.1, 27.8, and 21.3.

Step E: Preparation of 3(S)-(2,2-dimethoxyethylamino)-3-(6-methoxypyridin-3-yl)propionate tert butyl ester (1-6)

To a mixture of p-TSA salt 1-5(50 g; 0.118 mol), MeOH (300 mL), and glyoxal-1,1-dimethyl acetal (45 wt % in MTBE; 40 g; 0.165 mol) was slowly added a solution of NaBH$_3$CN (9.35 g; 0.141 mol; 95%) in MeOH (50 mL). The rate of addition was such that the temperature never exceeded 3.5° C. (over 50 min). The reaction mixture was allowed to warm up to ambient temperature. After reaction completion (4–5 hours, final batch temperature was 16° C.), ice was placed around the flask and aqueous NaHCO$_3$ (14.8 g in 200 mL of H$_2$O) solution was added slowly. The mixture was concentrated to 420 mL. Additional H$_2$O (200 mL) and EtOAc (500 mL) were added. The aqueous layer was separated and extracted with EtOAc (500 mL). The organic layers were combined, dried over MgSO$_4$, and concentrated to approximately 100 mL. The resulting solution was passed through a small silica gel pad followed by additional 300 mL of EtOAc. The fractions containing 1-6were combined and concentrated in vacuo to give 46.2 g of product 1-6(46.2 g; 90.4 wt %; 92%) as an oil. This compound was used for the next step without further purification. An authentic sample was prepared by silica gel column chromatography.
$^1$H NMR (250 MHz; CDCl$_3$): δ 8.08 (d, , J=2.4 Hz, 1H), 7.60 (dd, J=8.5 and 2.4 Hz, 1H), 6.73 (d, , J=8.5 Hz, 1H), 4.41 (t, J=5.4 Hz, 1H), 4.01 (dd, J=8.2 and 5.9 Hz, 1H), 3.92

(s, 3H), 3.89 (bs, 1H), 3.35 (s, 3H), 3.31 (s, 3H), 2.45-2.73 (m, 4H), and 1.39 (s, 9H).
$^{13}$C NMR (62.9 MHz; CDCl$_3$): δ 170.5, 163.7, 145.8, 137.4, 130.4, 119.5, 110.9, 103.5, 80.9, 56.8, 53.6, 53.3, 48.5, 43.8, and 27.9.

Step F: Preparation of 4-{3(S)-[2-tert-Butoxycarbonyl-1-(6-methoxy-pyridin-3-yl)-ethyl]-2-oxo-2,3-dihydro-imidazol-1-yl}-butyric acid methyl ester (1-7)

A solution of bis(trichloromethyl) carbonate (0.663 g; 2.24 mmol), acetal 1-6(2.0 g, 5.88 mmol) and triethylamine (2.0 mL) in anhydrous TBF (50 mL) was stirred at 0° C. for 30 minutes and at ambient temperature for 30 minutes. The excess phosgene was purged from the reaction mixture with argon. To the resulting suspension was added methyl 4-aminobutyrate hydrochloride (0.994 g; 6.47 mmol) and triethylamine (1.1 mL) at 5° C. The mixture was stirred at 40° C. for 6 hours then cooled to room temperature. 2M Aqueous sulfuric acid (8 mL) was added to the mixture and the mixture was stirred at ambient temperature for 16 hours. The mixture was poured into EtOAc, saturated NaHCO$_3$ added until basic. After extraction with EtOAc (3×), the organic layer was washed with brine, dried (MgSO$_4$) and concentrated in vacuo to give an oil. Purification by silica gel chromatography (EtOAc) gave 1-7.
$^1$H NMR (300 MHz; CDCl$_3$): δ 8.12 (d, 1H), 7.60 (dd, 1H), 6.72 (d, 1H), 6.21 (d, 1H), 6.19 (d, 1H), 6.72 (d, 1H), 5.60 (t, 1H), 3.92 (s, 31H), 3.67 (s, 3H), 3.64 (dt, 2H), 3.12 (dd, 1H), 2.98 (dd, 1H), 2.34 (t, 2H), 1.98 (quin, 2H), and 1.35 (s, 9H).

Step G: Preparation of of 4-{3(S)-[2-tert-butoxycarbonyl-1-(6-methoxy-pyridin-3-yl)-ethyl]-2-oxo-imidazolidin-1-yl}-butyric acid methyl ester (1-8)

A solution of 1-7(1.23 g) in methanol (70 mL) was degassed with argon and PtO$_2$ (200 mg) added. The mixture was placed on a Parr shaker with 58 psi hydrogen gas and shaken over 2 days. After purging with argon, the mixture was filtered through celite and the solvent removed in vacuo. Purification by silica gel chromatography (EtOAc:hexane 2:1) gave 1-8as a white solid.
$^1$H NMR (300 MHz; CDCl$_3$): δ 8.08 (d, 1H), 7.57 (dd, 1H), 6.72 (d, 1H), 5.21 (t, 1H), 3.91 (s, 3H), 3.63 (s, 3H), 3.4-2.8 (m, 8H), 2.32 (t, 2H), 1.81 (m, 2H), and 1.37 (s, 9H).

Step H: Preparation of 3(S)-(6-methoxy-pyridin-3-yl)-3-{2-oxo-3-[3-(1,4,5,6-tetrahydro-pyrimidin-2-ylcarbamoyl)-propyl]-imidazolidin-1-yl}-propionic acid tert-butyl ester (1-9)

A solution of 2-amino-3,4,5,6-tetrahydropyrimidine hydrochloride (386 mg; 2.85 mmol) in DMF (10 mL) was treated with sodium hydride (68 mg; 2.85 mmol) and stirred for 30 minutes. The imidazolidinone 1-8(300 mg; 0.71 mmol) was added and the mixture stirred for 16 hours. The solution was poured into saturated NaHCO$_3$ solution, extracted with EtOAc, washed with brine, dried (MgSO$_4$) and the solvent removed to give an oil. Purification by silica gel chromatography (CH$_2$Cl$_2$:MeOH:AcOH 100:20:5) afforded the title compound 1–9.
Mass spectrum: M+H found 489.2 calculated for C$_{24}$H$_{36}$N$_6$O$_5$+H is 489.3

Step I: Preparation of 3(S)-(6-methoxy-pyridin-3-yl)-3-{2-oxo-3-[3-(1,4,5,6-tetrahydro-pyrimidin-2-ylcarbamoyl)-propyl]-imidazolidin-1-yl}-propionic acid (1-10)

A solution of the ester 1–9(110 mg) in dichloromethane (10 mL) and trifluoroacetic acid (10 mL) were stirred at room temperature for 2 hours. The mixture was concentrated in vacuo, dissolved in water, frozen and lyophilized to give 1–10as a powder.
$^1$H NMR (300 MHz; CD$_3$OD): δ 8.11 (d, 1H), 7.70 (dd, 1H), 6.81 (d, 1H), 5.37 (t, 1H), 3.90 (s, 3H), 3.4-3.5 (m, 5H), 3.20 (m, 2H), 3.15 (m, 1H), 3.01 (d, 2H), 2.42 (t, 2H), 2.00 (quint, 2H), and 1.85 (quint, 2H).

Mass spectrum, exact mass: M+H found 433.2185 calculated for C$_{20}$H$_{28}$N$_6$O$_5$+H is 433.2194

Scheme 2

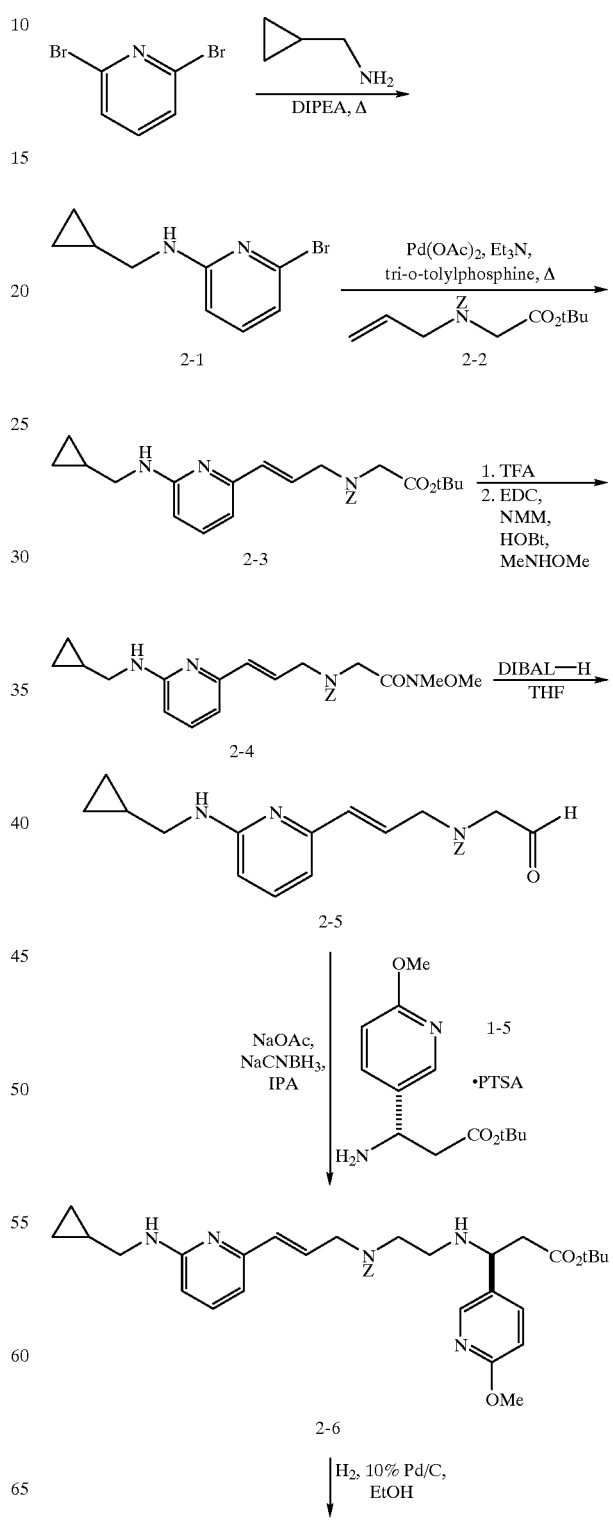

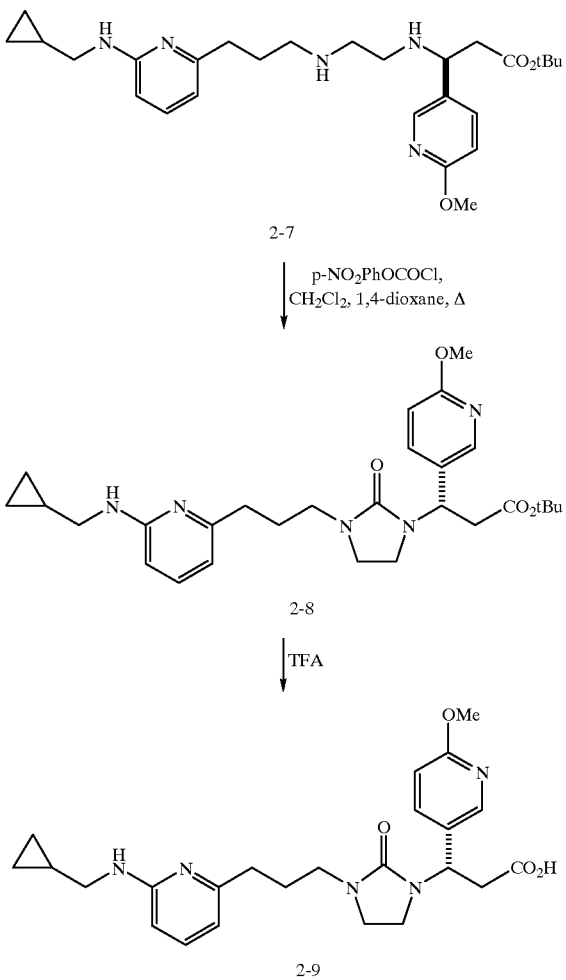

EXAMPLE 2

3-(3-{3-[6-(Cyclopropylmethyl-amino)-pyridin-2-yl]-propyl}-2-oxo-imidazolidin-1-yl)-3-(6-methoxy-pyridin-3-yl)-propionic acid (2-9)

Step A: (6-Bromo-pyridin-2-yl)-cyclopropylmethyl-amine (2-1)

A solution of 2,6-dibromopyridine (33.0 g, 139 mmol) and cyclopropanemethylamine (10.8 g, 153 mmol) in DIPEA (27 mL) was heated at reflux for 24 h in a sealed pressure tube. The reaction mixture was cooled, concentrated in vacuo, and the residue was partitioned between EtOAc (250 mL) and saturated aqueous NaHCO$_3$ (200 mL). The organic layer was washed with water (200 mL) followed by brine (200 mL) and dried (Na$_2$SO$_4$). The organic layer was filtered, concentrated in vacuo, and purified by flash chromatography (silica, 10% EtOAc/hexanes) affording 26 g of amine 2-1 as a white solid in 82% yield.

$^1$H NMR (300 MHz, CDCl$_3$) δ 7.22–7.26 (m, 1H), 6.70 (d, 1H), 6.26 (d, 1H), 4.78 (br s, 1H), 3.06–3.09 (m, 2H), 1.02–1.11 (m, 1H), 0.53–0.58 (m, 2H), 0.23–0.27 (m, 2H).

Step B: (Benzyloxycarbonyl-{3-[6-(cyclopropylmethyl-amino)-pyridin-2-yl]-allyl}-amino)-acetic acid tert-butyl ester (2-3)

A mixture of 2-1 (36.4 g, 160 mmol), 2-2 (53.9 g, 176 mmol), Pd(OAc)$_2$ (3.59 g, 16.0 mmol), and tri-o-tolylphosphine (9.76 g, 32.0 mmol) in Et$_3$N (22.2 mL, 160 mmol) under argon was heated at 100° C. for 12 h. The dark brown solution was cooled to room temperature, diluted with diethyl ether (750 mL) and washed with water (500 mL). The etheral layer was dried (Na$_2$SO$_4$), filtered, concentrated, and chromatographed (silica gel, 30% ethyl acetate/hexanes) to give 49.4 g of 2-3.

$^1$H NMR (400 MHz, CDCl$_3$) δ 7.30-7.39 (m, 6H), 6.22-6.63 (m, 4H), 5.16-5.18 (d, 2H), 4.60 (s, 1H), 4.15-4.21 (m, 2H), 3.87-3.96 (d, 2H), 3.13 (t, 2H), 1.37-1.44 (m, 9H), 1.06-1.12 (m, 1H), 0.53-0.56 (m, 2H), 0.23-0.27 (m, 2H).

Step C: {3-[6-(Cyclopropylmethyl-amino)-pyridin-2-yl]-allyl}-[(methox-methyl-carbamoyl)-methyl]-carbamic acid benzyl ester (2-4)

A solution of 2-3 (49.0 g, 109 mmol) in trifluoroacetic acid (50 mL) was stirred at 60° C. for 1 h. The solvent was evaporated and the residue was azeotroped (2×75 ml toluene). The residue was dissolved in CHCl$_3$/CH$_3$CN 1:1 (400 mL) and EDC (27.2 g, 142 mmol), HOBT (19.2 g, 142 mmol), NMM (60 mL, 546 mmol), and N,O-dimethylhydroxylamine (16.0 g, 164 mmol) were added. The slurry was stirred for 15 h and was concentrated in vacuo. The residue was dissolved in EtOAc (750 mL) and washed with saturated aqueous NaHCO$_3$, brine, dried (Na$_2$SO$_4$), filtered, and concentrated. Purification on silica gel afforded 30.8 g of 2-4 as a brown oil.

$^1$H NMR (400 MHz, CDCl$_3$) δ 7.30-7.39 (m, 6H), 6.24-6.65 (m, 4H), 5.13-5.18 (m, 2H), 4.63 (s, 1H), 4.15-4.28 (m, 3H), 3.69-3.74 (m, 2H), 3.43-3.51 (m, 1H), 3.10-3.21 (m, 6H), 1.06-1.12 (m, 1H), 0.53-0.56 (m, 2H), 0.23-0.27 (m, 2H).

Step D: {3-[6-(Cyclopropylmethyl-amino)-pyridin-2-yl]-allyl}-(2-oxo-ethyl)-carbamic acid benzyl ester (2-5)

To a stirred solution of 2-4 (32.0 g, 72.9 mmol) in THF (200 mL) at −78° C. was added DIBAL-H (1.0M/heptanes, 109 mL, 109 mmol) dropwise over 30 minutes. After 1.5 h the solution was warmed to room temperature and quenched by the careful addition of MeOH (20 mL). A 1.0M Aqueous Rochelle salt solution (200 mL) was added and the solution stirred for an additional 1 h. Et$_2$O (600 mL) was added and after 30 minutes the organic layer was separated and dried (Na$_2$SO$_4$). Concentration in vacuo afforded 25 g of crude aldehyde 2-5.

$^1$H NMR (300 MHz, CDCl$_3$) δ 9.60 (d, 1H), 7.26-7.39 (m, 6H), 6.25-6.65 (m, 4H), 5.15-5.20 (m, 2H), 4.62 (s, 1H), 4.10-4.19 (m, 2H), 3.45-3.53 (m, 2H), 3.06-3.14 (m, 2H), 1.06-1.12 (m, 1H), 0.53-0.55 (m, 2H), 0.25-0.27 (m, 2H).

Step E: 3-[2-(Benzyloxycarbonyl-{3-[6-(cyclopropylmethyl-amino)pyridin-2-yl]-allyl}-amino)-ethylamino]-3-(6-methoxy-pyridin-3-yl)-propionic acid tert-butyl ester (2-6)

To a solution of aldehyde 2-5 (25.0 g, 65.8 mmol) in isopropanol (400 mL) was added β-alanine 1-5 (27.9 g, 65.8 mmol), NaOAc (54.0 g, 658 mmol), and 4 Å molecular sieves. The solution stirred for 20 minutes and was cooled to 0° C. and NaCNBH$_3$ (12.4 g, 197 mmol) was added in one portion. The ice bath was removed and the solution stirred for 14 h at room temperature. 1N HCl was added to bring the pH to 2. After 10 minutes of stirring, EtOAc (700 mL) was added and the pH was adjusted to 11 with 10% aqueous K$_2$CO$_3$. The organic layer was separated, dried (Na$_2$SO$_4$), filtered, concentrated in vacuo, and purified on silica gel (75:20:5 CHCl$_3$:EtOAc:MeOH) to give 29.3 g of 2-6.

$^1$H NMR (400 MHz, CDCl$_3$) δ 8.11 (d, 1H), 7.28-7.38 (m, 6H), 6.25-6.72 (m, 6H), 5.12-5.18 (m, 2H), 4.63 (br s, 1H), 4.34-4.38 (m, 1H), 3.92 (s, 3H), 3.32-3.50 (m, 2H), 3.13 (t, 2H), 2.41-2.52 (m, 7H), 1.39 (d, 9H), 1.06-1.12 (m, 1H), 0.53-0.55 (m, 2H), 0.25-0.27 (m, 2H).

Step F: 3-(2-{3-[6-(Cyclopropylmethyl-amino)-pyridin-2-yl]-propylamino}-ethylamino)-3-(6-methoxy-pyridin-3-yl)-propionic acid tert-butyl ester (2-7)

A mixture of 2-6 (29.0 g, 47.0 mmol) and 10% Pd/C (7.25 g) in EtOH (500 mL) was stirred under a balloon of hydrogen for 18 h. Filtration through celite and evaporative removal of the solvent followed by purification on silica gel (90:10:1 CHCl$_3$:MeOH:NHOH) afforded 13 g of 2-7.
$^1$H NMR (300 MHz, CDCl$_3$) δ 8.06-8.08 (m, 1H), 7.56-7.60 (m, 1H), 7.35 (t, 1H), 6.72-6.75 (m, 1H), 6.42-6.47 (m, 1H), 6.19 (d, 1H), 4.66 (br s, 1H), 3.97-4.03 (m, 1H), 3.93 (s, 3H), 3.07 (t, 2H), 2.46-2.78 (m, I1H), 1.81-1.99 (m, 3H), 1.39 (d, 9H), 1.06-1.12 (m, 1H), 0.53-0.55 (m, 2H), 0.25-0.27 (m, 2H).

Step G: 3-(3-}3-[6-(Cyclopropylmethyl-amino)-pyridin-2-yl]-propyl}-2-oxo-imidazolidin-1-yl)-3-(6-methoxy-pyridin-3-yl)-propionic acid tert-butyl ester (2-8)

To a solution of diamine 2-7 (12.5 g, 25.8 mmol) and DIPEA (13.5 mL, 77.5 mmol) in CH$_2$Cl$_2$ (750 mL) at 0° C. was added p-NO$_2$PhOCOCl (5.47 g, 27.1 mmol) in 4 portions. The resulting mixture was warmed to room temperature and 1,4-dioxane (750 mL) was added and refluxed for 6 h. After cooling, the solution was washed with 10% K$_2$CO$_3$ (3×400 mL) then brine. The organic layer was dried (Na$_2$SO$_4$), filtered, concentrated in vacuo, and purified by flash chromatography (silica, 50% EtOAc/hexanes) affording 9.0 g of cyclic urea 2-8.
$^1$H NMR (400 MHz, CDCl$_3$) δ 8.08 (d, 1H), 7.58 (dd, 1H), 7.35 (t, 1H), 6.71 (d, 1H), 6.41 (d, 1H), 6.17 (d, 1H), 5.38-5.43 (t, 1H), 4.60 (br s, 1H), 3.91 (s, 3H), 3.19-3.32 (m, 5H), 3.06 (t, 2H), 2.92-2.98 (m, 1H), 2.59 (t, 2H), 1.83-1.92 (m, 2H), 1.37 (s, 9H), 1.06-1.12 (m, 1H), 0.53-0.55 (m, 2H), 0.25-0.27 (m, 2H).

Step H: 3-(3-{3- [6-(Cyclopropylmethyl-amino)-pyridin-2-yl]-propyl}-2-oxo-imidazolidin-1-yl)-3-(6-methoxy-pyridin-3-yl)-propionic acid (2-9)

A solution of 2-8 (8.90 g, 17.4 mmol) in trifluoroacetic acid (15 mL) was stirred at 60° C. for 20 minutes. The solvent was evaporated and the residue was azeotroped (2×75 ml toluene). Purification on silica gel (90:10:1 CHCl$_3$:MeOH:NH$_4$OH) afforded 7.9 g of 2-9.
$^1$H NMR (400 MHz, CDCl$_3$) δ 8.10 (d, 1H), 7.52-7.58 (m, 2H), 6.70 (d, 1H), 6.38-6.44 (m, 2H), 5.70 (dd, 1H), 3.92 (s, 3H), 3.41-3.67 (m, 4H), 3.06-3.23 (m, 3H), 2.84-3.00 (m, 3H), 2.71-2.79 (m, 2H), 2.64 (dd, 1H) 1.83-1.92 (m, 2H), 1.37 (s, 9H), 1.12-1.18 (m, 1H), 0.56-0.61 (m, 2H), 0.26-0.34 (m, 2H).

Scheme 3

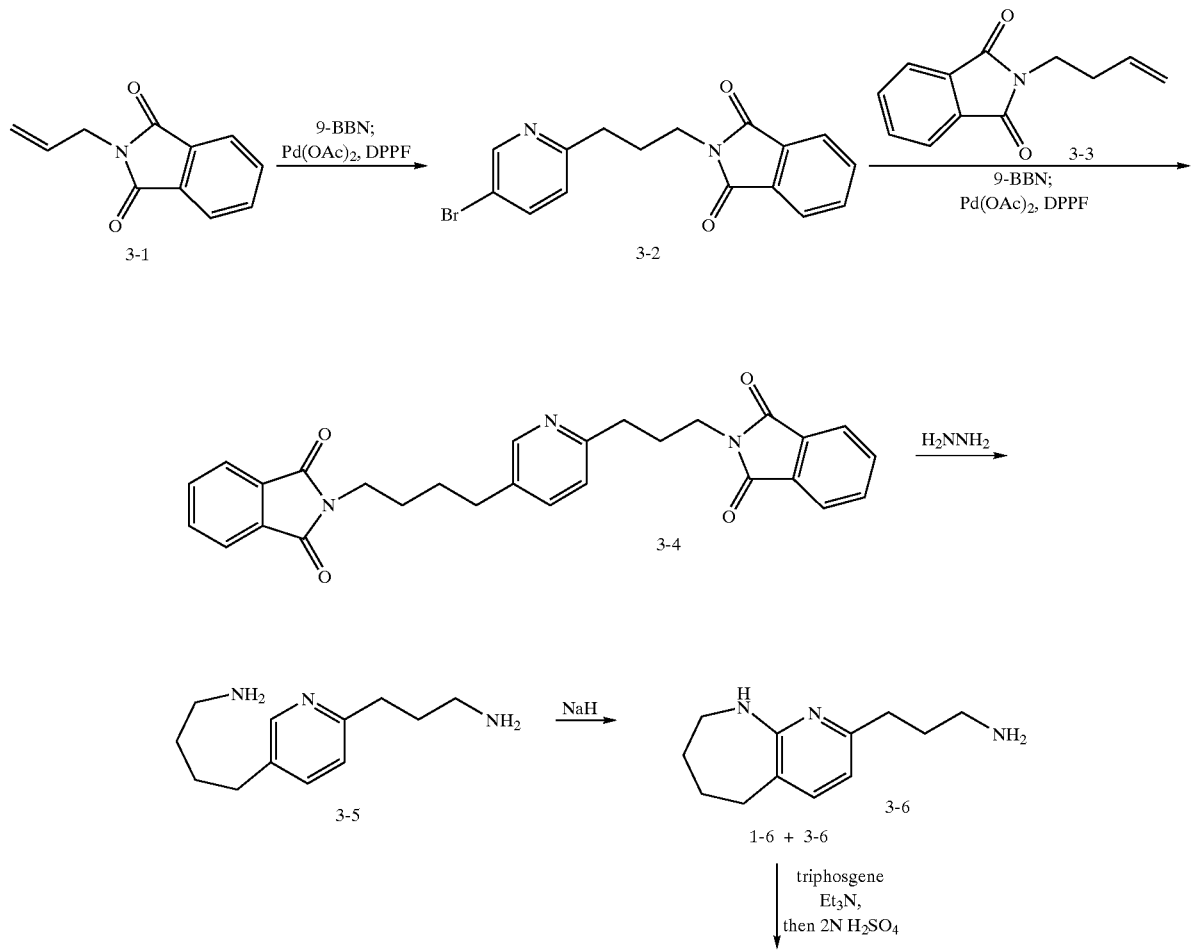

-continued

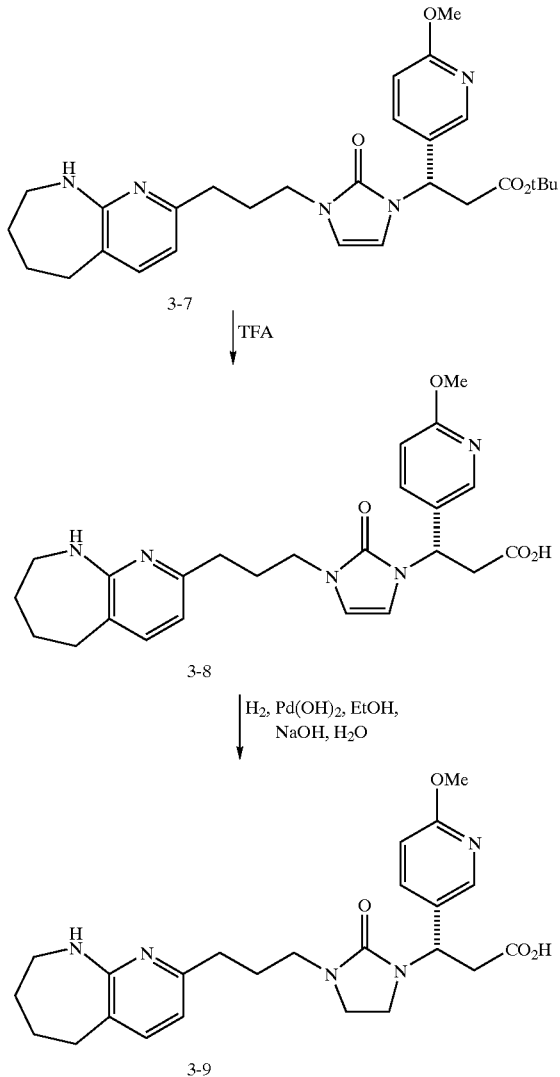

EXAMPLE 3

3(S)-(6-Methoxy-pyridin-3-yl)-3-{2-oxo-3-[3-(6,7,8,9-tetrahydro-5H-pyrido[2,3-b]azepin-2-yl)-propyl]-imidazolidin-1-yl}-propionic acid (3-9)

Step A: 2-[3-(5-Bromo-pyridin-2-yl)-propyl]-isoindole-1,3-dione (3-2)

To a stirred solution of 2-allyl-isoindole-1,3-dione (3-1) (18.9 g, 101 mmol) in degassed TBF (100 mL) at 0° C. was added dropwise a solution of 9-BBN (243 mL of 0.5M in THF, 121 mmol) and the mixture stirred for 18 hours at ambient temperature. $K_2CO_3$ (24 g, 172 mmol) and 2,5-dibromopyridine (30 g, 126 mmol) were added, followed by a premixed and aged (70° C. for 30 min) suspension of $Pd(OAc)_2$ (2.6 g, 11.5 mmol) and DPPF (7 g, 12.6 mmol) in degassed DMF (100 mL). The resulting mixture was stirred for 18 hours at 70° C., cooled, diluted with ethyl acetate, washed with water and brine, dried over $MgSO_4$, and concentrated. To the stirring residue dissolved in TUF (500 mL) were added water (150 mL) and $NaHCO_3$ (33 g) and after 10 minutes, $NaBO_3 \cdot H_2O$ (55 g). After vigorous stirring for 30 minutes, the mixture was diluted with ethyl acetate, washed with water and brine, dried over $MgSO_4$, and concentrated to an oil. The residue was chromatographed on silica gel (10–20% EtOAc/hexane) to give 13 g of 3-2 as a colorless oil.

TLC $R_f$=0.21 (silica, 20% EtOAc/hexane).

$^1$H NMR (400 MHz, $CDCl_3$) δ 8.51 (d, 1H, J=2 Hz), 7.82 (m, 2H), 7.71 (m, 3H), 7.08 (d, 2H, J=8 Hz), 3.75 (t, 2H, J=7 Hz), 2.81 (t, 2H, J=7 Hz), 2.17 (m, 2H).

Step B: 2-But-3-enyl-isoindole-1,3-dione (3-3)

To a stirred solution of 4-bromo-1-butene (20 g, 148 mmol) in DMF (150 mL) was added potassium phthalimide (25 g, 133 mmol) and the mixture stirred for 18 hours at 70° C. After cooling to RT, the mixture was diluted with ether, washed with water and brine, dried over $MgSO_4$, and concentrated to give 22.1 g of 3-3 as a white solid.

$^1$H NMR (400 MHz, $CDCl_3$) δ 7.85 (m, 2H), 7.72 (m, 2H), 5.82 (m, 1H), 5.08 (m, 2H), 3.77 (t, 2H, J=7 Hz), 2.44 (m, 2H).

Step C: 2-(3-{5-[4-(1,3-dioxo-isoindol-2-yl)-butyl]-pyridin-2-yl}-propyl)-isoindole-1,3-dione (3-4)

To a stirred solution of 3-3 (9.1 g, 45.4 mmol) in degassed THF (50 mL) at 0° C. was added dropwise a solution of 9-BBN (110 mL of 0.5M in THF, 55 mmol) and the mixture stirred for 18 hours at ambient temperature. $K_2CO_3$ (10.8 g, 77.4 mmol) and 3-2 (5.0 g, 17.4 mmol) were added, followed by a premixed and aged (70° C. for 30 min) suspension of $Pd(OAc)_2$ (1.2 g, 5.2 mmol) and DPPF (3.2 g, 5.6 mmol) in degassed DMF (50 mL). The resulting mixture was stirred for 18 hours at 70° C., cooled, diluted with ethyl acetate, washed with water and brine, dried over MgSO$_4$, and concentrated. The residue was chromatographed on silica gel (40–50% EtOAc/hexane) to give 6.2 g of 3-4 as a white solid.

TLC R$_f$=0.19 (silica, 50% EtOAc/hexane).

$^1$H NMR (400 MHz, CDCl$_3$) δ 8.31 (s, 1H), 7.84 (m, 4H), 7.73 (m, 4H), 7.38 (d, 1H, J=8 Hz), 7.08 (d, 1H, J=8 Hz), 3.73 (m, 4H), 2.72 (t, 2H, J=7 Hz), 2.59 (t, 2H, J=7 Hz), 2.13 (m, 2H), 1.66 (m, 2H), 1.61 (m, 2H).

Step D: 4-[6-(3-Amino-propyl)-pyridin-3-yl]-butyl amine (3-5)

A mixture of 3-4 (14 g, 30.7 mmol) and hydrazine (5 mL) in ethanol (500 mL) was heated at reflux for 5 hours. The mixture was cooled and concentrated to ⅓ volume, diluted with 300 mL MTBE, and filtered. The filtrate was concentrated to give 7.1 g of 3-5 as a brown oil, contaminated with a small amount of phthalhydrazide.

$^1$H NMR (400 MHz, CDCl$_3$) δ 8.26 (s, 1H), 7.46 (d, 1H, J=8 Hz), 7.06 (d, 1H, J=8 Hz), 2.77 (t, 2H, J=7 Hz), 2.67 (m, 4H), 2.60 (t, 2H, J=7 Hz), 2.22 (br s, 4H), 1.84 (m, 2H), 1.63 (m, 2H), 1.48 (m, 2H).

Step E: 3-(6,7,8,9-Tetrahydro-5H-pyrido[2,3-b]azepin-2-yl)-propylamine (3-6)

A mixture of 3-5 (3.0 g, 14.5 mmol) and NaH (1.7 g of a 60% weight dispersion in mineral oil, 47 mmol) in xylenes (100 mL) was purged with argon for 30 min, and then heated at reflux for 72 hours. The mixture was cooled, quenched with ethanol, diluted with 10% aqueous potassium carbonate and extracted with ethyl acetate. The organics were dried over MgSO$_4$ and concentrated to an oil. The residue was chromatographed on silica gel (15:10:1:1 EtOAc/EtOH/NH$_4$OH/H$_2$O) to give 800 mg of 3-6 as a yellow oil.

TLC R$_f$=0.20 (silica, 15:10:1:1 EtOAc/EtOH/NH$_4$OH/H$_2$O).

$^1$H NMR (400 MHz, CDCl$_3$) δ 7.24 (d, 1H, J=7 Hz), 6.54 (d, 1H, J=7 Hz), 4.69 (br s, 1H), 3.13 (m, 2H), 2.72 (t, 2H, J=7 Hz), 2.64 (m, 4H), 2.7-1.70 (m, 6H), 1.65 (m, 2H).

Step F: 3(S)-(6-Methoxy-pyridin-3-yl)-3-{2-oxo-3-[3-(6,7,8,9-tetrahydro-5H-pyrido[2,3-b]azepin-2-yl)-propyl]-2,3-dihydro-imidazol-1-yl}-propionic acid tert-butyl ester (3-7)

To a solution of triphosgene (0.246 g, 0.804 mmol) in THF (5 mL) at 0° C. was added a mixture of 1-6 (0.78 g, 2.29 mmol), triethylamine (0.36 mL, 3.09 mmol) and THF (1 mL) over 10 minutes. After 30 minutes, the reaction was allowed to warm to ambient temperature and stir for 1 hour. The mixture was then purged with argon for 30 minutes, and to it was added a mixture of 3-6 (0.435 g, 2.52 mmol), triethylamine (0.36 mL, 3.09 mmol) and THF (5 mL). The mixture was then heated at 0° C. for 2 hours, allowed to cool to ambient temperature. 2M H$_2$SO$_4$ (2.5 mL) was then added, and the mixture stirred for 15 hours. The reaction was then quenched with a 10% w/v solution of K$_2$CO$_3$ (10 mL), diluted with ethyl acetate, washed with water and brine, dried over MgSO$_4$, and concentrated to give 850 mg of 3-7 as a yellow oil, used crude in the next step.

Step G: 3(S)-(6-Methoxy-pyridin-3-yl)-3-[2-oxo-3-[3-(6,7,8,9-tetrahydro-5H-pyrido[2,3-b]azepin-2-yl)-propyl]-2,3-dihydro-imidazol-1-yl}-propionic acid (3-8)

To a solution of 3-7 (0.85 g, 1.67 mmol) in dichloromethane (10 mL) was added anhydrous TFA (5 mL). After 4 hours, the mixture was concentrated, diluted with toluene, and re-concentrated. The residue was chromatographed on silica gel (15:10:1:1 to 15:10:1:1 EtOAc/EtOH(NH$_4$OH/H$_2$O) to give 600 mg of 3-8 as a white solid.

TLC R$_f$=0.19 (silica, 15:10:1:1 EtOAc/EtOH/NH$_4$OH/H$_2$O).

$^1$H NMR (400 MHz, CD$_3$OD) δ 8.16 (d, 1H, J=2 Hz), 7.74 (dd, 1H, J=3,9 Hz), 7.52 (d, 1H, J=8 Hz), 6.80 (d, 1H, J=9 Hz), 6.63 (d, 1H, J=7 Hz), 6.55 (d, 1H, J=3 Hz), 6.50 (d, 1H, J=3 Hz), 5.64 (m, 1H), 3.90 (s, 3H), 3.76 (m, 1H), 3.62-3.41 (m, 4H), 3.08-2.82 (m, 4H), 2.69 (m, 1H), 2.50 (m, 1H), 2.09-1.86 (m, 5H).

Step H: 3(S)-(6-Methoxy-pyridin-3-yl)-3-{2-oxo-3-[3-(6,7,8,9-tetrahydro-5H-pyrido[2,3-b]azepin-2-yl)-propyl]-imidazolidin-1-yl}-propionic acid (3-9)

A mixture of 3-8 (0.40 g, 0.886 mmol), 20% Pd(OH)$_2$ (0.40g), 1N NaOH (2 mL), and ethanol (20 mL) was shaken under 65 psig hydrogen in a Parr apparatus for 18 hours. The mixture was filtered through celite, and the filtrate concentrated. The residue was chromatographed on silica gel (25:10:1:1 to 15:10:1:1 EtOAc/EtOH/NH$_4$OH/H$_2$O) to give 350 mg of 3-9 as a white solid.

TLC R$_f$=0.19 (silica, 15:10:1:1 EtOAc/EtOH/NH$_4$OH/H$_2$O).

$^1$H NMR (400 MHz, CD$_3$OD) δ 8.09 (d, 1H, J=2 Hz), 7.63 (m, 1H), 7.52 (d, 1H, J=7 Hz), 6.80 (d, 1H, J=8 Hz), 6.64 (d, 1H, J=8 Hz), 5.44 (m, 1H), 3.90 (s, 3H), 3.61 (m, 1H), 3.50 (m, 4H), 3.18 (m, 2H), 2.93 (m, 2H), 2.72 (m, 2H), 2.59 (m, 4H), 2.10-1.76 (m, 5H).

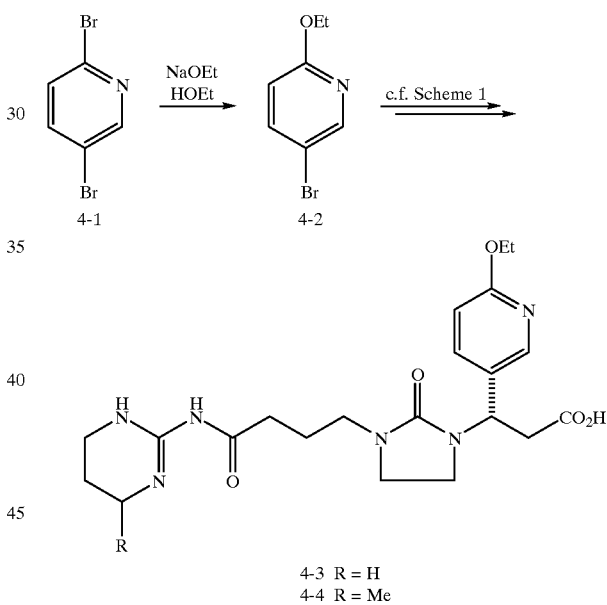

Scheme 4

EXAMPLE 4

3(S)-(6-Ethoxypyridin-3-yl)-3-{2-oxo-3-[3-(1,4,5,6-tetrahydro-pyrimidin-2-ylcarbamoyl)-propyl]-imidazolidin-1-yl}-propionic acid (4-3)

Step A: Preparation of 3-bromo-6-ethoxypyridine (4-2)

A solution of NaOEt in EtOH (21%; 157 mL, 422 mmol) was added to 2,5-dibromopyridine (4-1) (20 g; 84.4 mmol) and the mixture heated to 80° C. for 16 hours. After cooling, the mixture was poured into water, extracted twice with EtOAc, washed with water then brine, dried (MgSO$_4$) and concentrated under reduced pressure to give crude product 4-2 as a solid.

$^1$H NMR (300 MHz; CDCl$_3$): δ 1.38 (3H, t), 4.33 (2H, q), 6.63 (1H, d), 7.62 (1H, dd), 8.19 (1H, d).

Step B: Preparation of 3(S)-(6-ethoxy-pyridin-3-yl)-3-{2-oxo-3-[3-(1,4,5,6-tetrahydro-pyrimidin-2-ylcarbamoyl)-propyl]-imidazolidin-1-yl}-propionic acid (4-3)

Following the procedure described for Example 1, but using 4-2 as starting material, the title compound 4-3 was prepared as a TFA salt.

Mass spectrum: found 447.1; calculated (M+H)=447.2.

$^1$H NMR (300 MHz; CD3OD): δ 1.36 (3H, t), 1.85 (2H, quin), 2.00 (2H, quin), 2.41 (2H, t), 3.00 (2H, d), 3.09 (1H, q), 3.22 (2H, m), 3.35 (2H, m), 3.47 (5H, m), 4.31 (2H, q), 5.37 (1H, t), 6.81 (1H, d), 7.72 (1H, dd), 8.09 (1H, d).

EXAMPLE 5

3(S)-(6-Ethoxy-pyridin-3-yl)-3-}2-oxo-3-[3-(4-methyl-1,4,5,6-tetrahydropyrimidin-2-ylcarbamoyl)-propyl]-imidazolidin-1-yl}-propionic acid (4-4)

Following the procedure described for Example 1, but using 4-2 and 2-amino-4-methyl-1,4,5,6-tetrahydropyrimidine (obtained by hydrogenation of 2-amino-4-methylpyrimidine hydrochloride over Pd(OH)$_2$ in EtOH) as starting material, the title compound 4-4 was prepared as a TFA salt.

Mass spectrum: found 461.1; calculated (M+H)=461.3.

$^1$H NMR (300 MHz; CD$_3$OD): δ 1.33 (3H, dd), 1.36 (3H, t), 1.75 (1H, m), 1.85 (2H, quin), 2.1 (1H, m), 2.42 (2H, t), 3.01 (2H, d), 3.09 (1H, m), 3.22 (2H, m), 3.35 (2H, m), 3.4-3.6 (3H, m), 3.74 (11H, m), 4.31 (2H, q), 5.36 (1H, t), 6.80 (1H, d), 7.71 (1H, dd), 8.09 (1H, d).

EXAMPLE 6

3(S)-(Dihydrobenzofuran-6-yl)-3-{2-oxo-3-[3-(1,4,5,6-tetrahydro-pyrimidin-2-ylcarbamoyl)-propyl]-imidazolidin-1-yl}-propionic acid (5-2)

Following the procedure described for Example 1, but using 5-1 (Coleman et al, *Tetrahedron Lett.*, 41:5803–5806 (2000)) as starting material, the title compound 5-2 was prepared as a TFA salt.

Mass spectrum: found 444.2; calculated (M+H)=444.2.

$^1$H NMR (500 MHz; CD$_3$OD): δ 1.85 (2H, m), 2.01 (2H, quin), 2.43 (2H, t), 2.95 (2H, d), 3.04 (1H, q), 3.17 (2H, t), 3.23 (2H, m), 3.30 (2H, m), 3.40 (1H, m), 3.46 (4H, t), 4.53 (2H, t), 5.36 (1H, t), 6.71 (1H, d), 6.79 (1H, dd), 7.17 (1H, d).

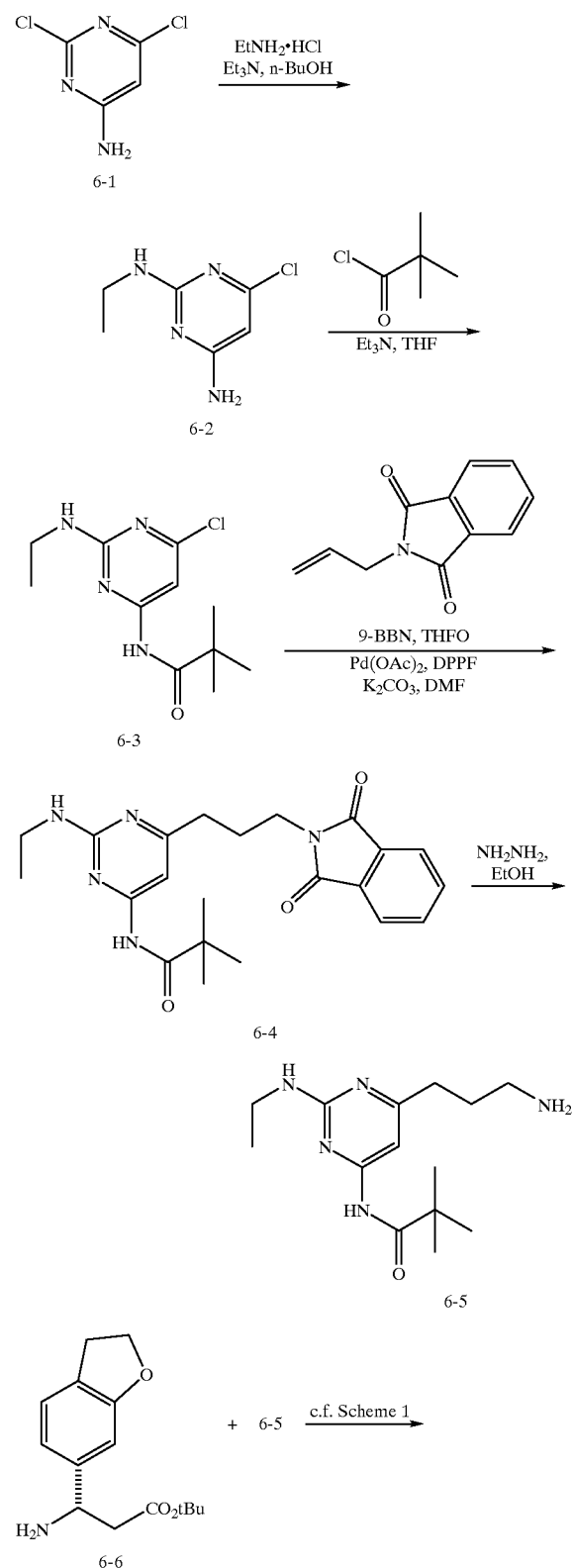

Scheme 6

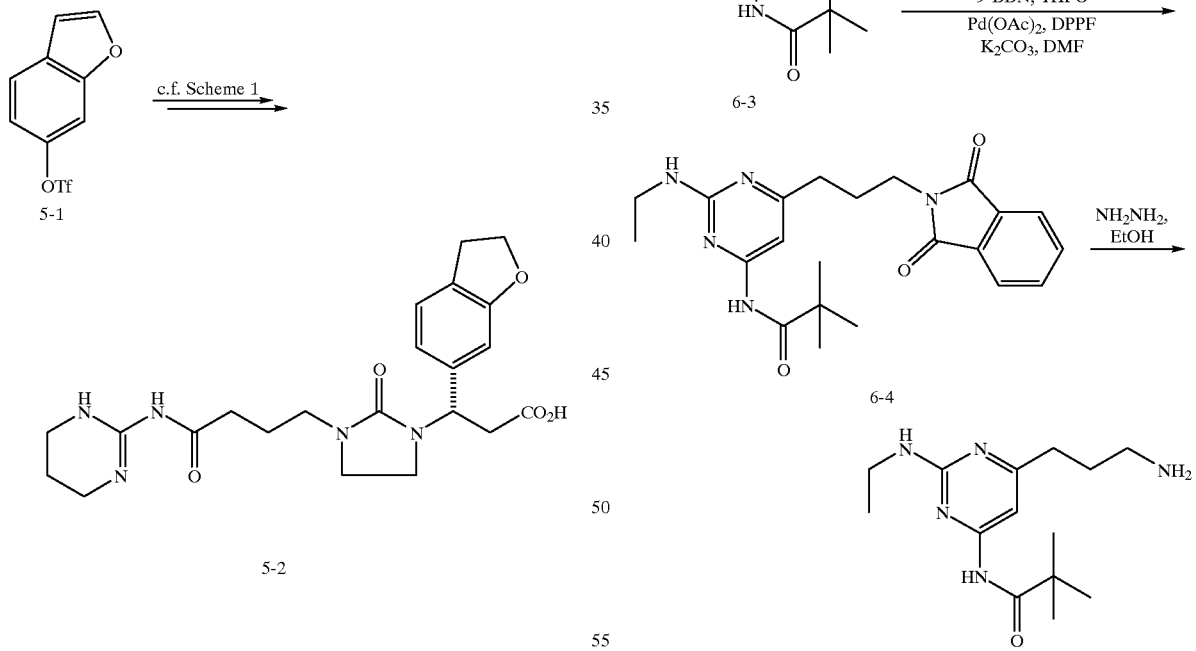

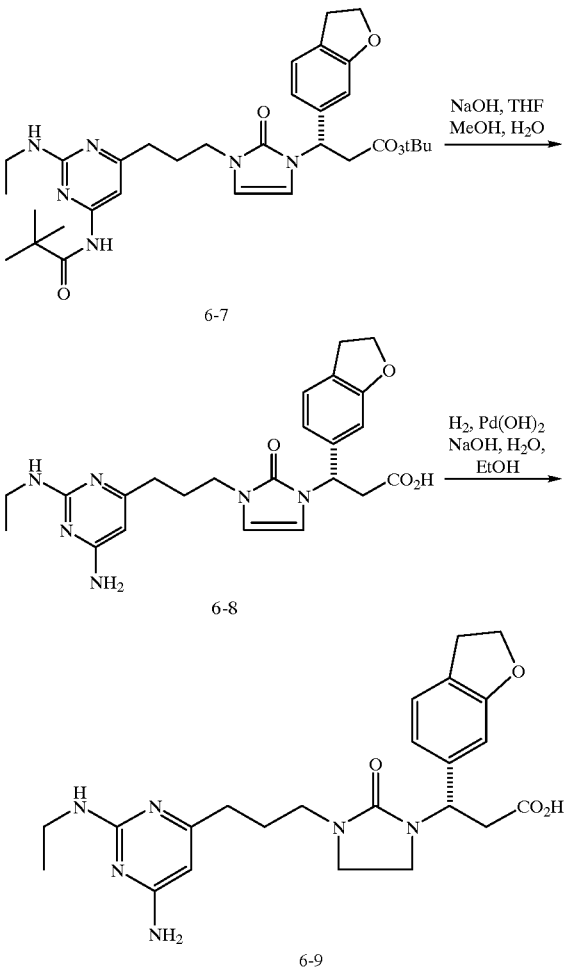

EXAMPLE 7

3(S)-(Dihydrobenzofuran-6-yl)-3-{2-oxo-3-[3-(4-amino-2-ethylaminopyrimidin-6-yl)-propyl]-imidazolidin-1-yl}-propionic acid (6-9)

Step A: 4-Amino-6-chloro-2-ethylaminopyrimidine (6-2)

A mixture of 2,6-dichloro-4-aminopyrimidine 6-1 (4.8 g, 29.3 mmol), ethylamine hydrochloride (7.0 g, 85.8 mmol), Et₃N (20 mL, 144 mmol) and n-butanol (150 mL) was heated to 90° C. for 6 hours. After cooling, the solvent was removed in vacuo and the residue partitioned between saturated Na₂CO₃ solution and EtOAc. The EtOAc layer was washed with brine, dried (MgSO₄) and concentrated to give an orange solid. Purification by column chromatography (EtOAc/hexane 1:1) gave the title compound 6-2 as a white solid.

¹H NMR (400 MHz, CDCl₃): 5.78 (1H, s), 5.03 (1H, br s), 4.75 (2H, br s), 3.37 (2H, quintet), 1.18 (3H, t).

Step B: 4-Pivaloylamino-6-chloro-2-ethylaminopyrimidine (6-3)

A mixture of the pyrimidine 6-2 (3.76 g, 21.8 mmol), pivaloyl chloride (10.7 mL, 87 mmol), Et₃N (15.2 mL, 109 mmol) and TBF (80 mL) was stirred at room temperature for 24 hours. A further 3 mL of pivaloyl chloride and 4 mL of Et₃N was added and the mixture stirred for another 24 hours. The solution was poured into saturated Na₂CO₃, extracted twice with EtOAc, washed with brine, dried (MgSO₄) and filtered through a pad of silica gel. Removal of the solvent afforded an orange solid. Trituration with ether/hexane (~20:1) and filtration provided the title compound 6-3 as a white solid.

¹H NMR (400 MHz, CDCl₃): 7.77 (1H, br s), 7.5 (1H, s), 5.06 (1H, br s), 3.40 (2H, quintet), 1.30 (9H, s), 1.20 (3H, t).

Step C: 3-(4-Pivaloylamino-2-ethylaminopyrimidin-6-yl)propyl-1-N-phthalimide (6-4)

A solution of 9-BBN (0.5M THF; 14.6 mL, 7.28 mmol) was added to N-allylphthalimide (1.13 g, 6.06 mmol) and stirred for 16 hours at room temperature. To this was added the pyrimidine 6-3 (1.4 g, 5.46 mmol), Pd(OAc)2 (136 mg, 0.61 mmol), DPPF (336 mg, 0.61 mmol), K₂CO₃ (1.26 g, 9.1 mmol) and DMF (15 mL). The mixture was degassed with nitrogen for 15 minutes, then heated to 90° C. for 16 hours before removal of most of the solvent in vacuo. To the residue was added saturated Na₂CO₃ (30 mL), EtOAc (10 mL) and NaBO₃.4H₂O and the mixture stirred for 3 hours. After pouring into water, the solution was extracted twice with EtOAc, washed with water then brine, dried (MgSO₄) filtered through a pad of silica gel and then concentrated to give a dark brown oil. Purification by silica gel chromatography (hexane/EtOAc 3:2 then 1:2) afforded the title compound 6-4 as an oil.

Mass spectrum: found 410. 1; calculated (M+H)=410.2.

Step D: 3-(4-Pivaloylamino-2-ethylaminopyrimidin-6-yl)-1-propylamine (6-5)

A solution of the phthalimide 6-4 (920 mg, 2.25 mmol) and hydrazine (0.420 mL, 13.5 mmol) in EtOH was heated to 50° C. for 2 hours then cooled and 10 "mL of MTBE was added. The resulting solid was removed by filtration and the filtrate concentrated to give the crude product. Purification by silica gel chromatography (CHCl₃/EtOAc/MeOH 8:1:1 then 5% MeOH in CHCl3 saturated with NH₃) gave the title compound 6-5.

¹H NMR (400 MHz, CDCl₃): 7.73 (1H, br s), 7.34 (1H, s), 4.88 (1H, br s), 3.39 (2H, m), 2.75 (2H, m), 2.59 (2H, m), 1.83 (2H, m), 1.3 (9H, s), 1.2 (3H, t).

Step E: 3(S)-(dihydrobenzofuran-6-yl)-3-{2-oxo-3-[3-(4-pivaloylamino-2-ethylaminopyrimidin-6-yl)-propyl]-2,3-dihydro-imidazol-1-yl}-propionic acid t-butyl ester (6-7)

The amine 6-5 and the amine 6-6 (prepared from 5-1 according to the procedures described in Example 1) were coupled using the procedure described for Example 1 compound 1-7 to give the title compound 6-7.

Mass spectrum: found 593.3; calculated (M+H)=593.3.

Step F: 3(S)-(dihydrobenzofuran-6-yl)-3-{2-oxo-3-[3-(4-amino-2-ethylaminopyrimidin-6-yl)-propyl]-2,3-dihydro-imidazol-1-yl}-propionic acid (6-8)

The ester 6-7 (870 mg, 1.47 mmol) in THF (20 mL), MeOH (20 mL) and H₂O (20 mL) was treated with 1N NaOH (12 μL, 12 mmol) and heated to 70° C. for 8 hours. The solution was cooled, diluted with water and then neutralized with 3N HCl. Purification by preparative "PLC (C-18 column; water/acetonitrile +0.1% TFA; gradient elution) followed by lyophilization afforded the title compound 6-8 as a TFA salt.

Mass spectrum: found 453.1; calculated (M+H)=453.2.

¹H NMR (500 MHz; CD₃OD): δ 1.22 (3H, t), 1.99 (2H, m), 2.47 (2H, m), 3.1-3.2 (4H, m), 3.45 (2H, q), 3.7 (2H, m), 4.52 (2H, t), 5.61 (1H, dd), 5.92 (1H, s), 6.54 (1H, d), 6.68 (1H, d), 6.72 (1H, s), 6.82 (1H, dd), 7.16 (1H, d).

Step G: 3(S)-(dihydrobenzofuran-6-yl)-3-{2-oxo-3-1 3-(4-amino-2-ethylaminopyrimidin-6-yl)-propyl]-imidazolidin-1-yl}-propionic acid (6-9)

A solution of the acid 6-8 (520 mg, 1.15 mmol) and 1N NaOH (5 mL) in EtOH (25 mL) and water (10 mL) was hydrogenated over Pd(OH)₂ on carbon (20%; 2 g) at 65 psi for 4 days. The mixture was filtered through celite, the solvent removed and then the residue was neutralized with 3N HCl. Purification by preparative HPLC (C-18 column; water/acetonitrile +0.1% TFA; gradient elution) followed by lyophilization afforded the title compound 6-9 as a TFA salt.

Mass spectrum: found 455.2; calculated (M+H)=455.2.

¹H NMR (500 MHz; CD₃OD): δ 1.22 (3H, t), 1.83 (2H, m), 2.50 (2H, t), 2.95 (2H, m), 3.06 (2H, q), 3.17 (2H, t), 3.23 (2H, m), 3.33 (2H, m), 3.45 (3H, m), 4.53 (2H, t), 5.38 (1H, t), 5.93 (1H, s), 6.72 (1H, dd), 6.81 (1H, dd), 7.17 (1H, d).

Scheme 7

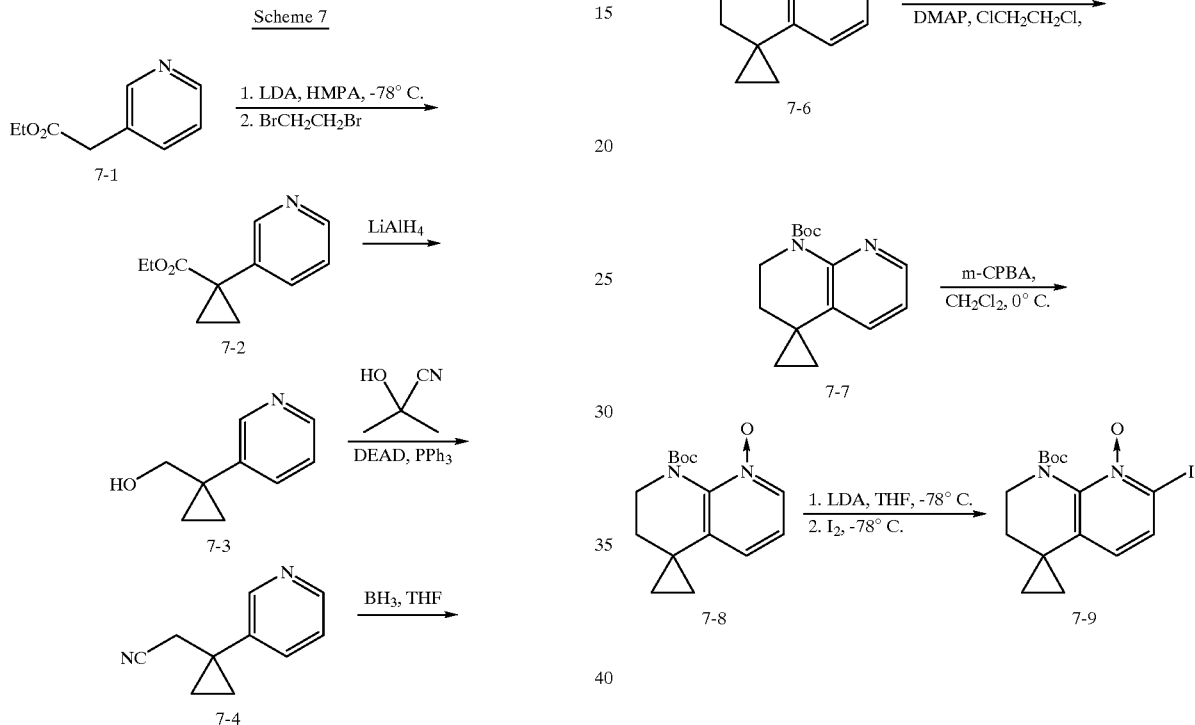

Scheme 8

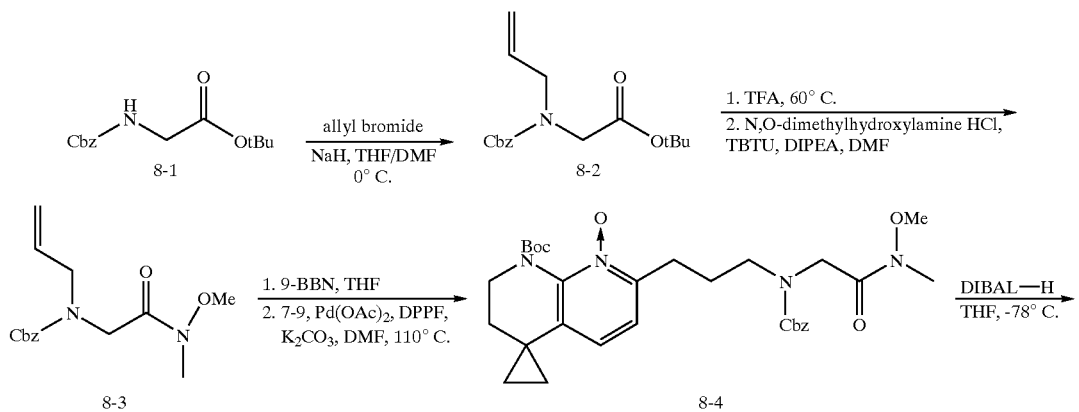

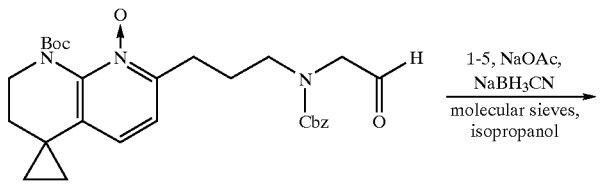

8-5

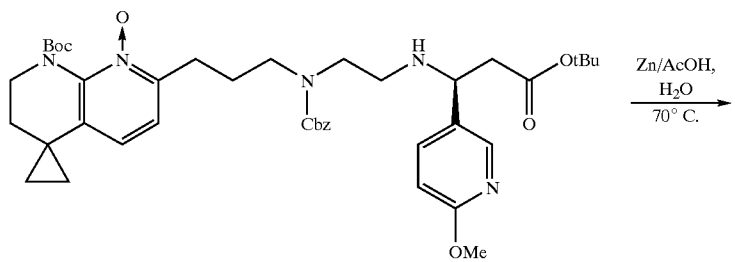

8-6

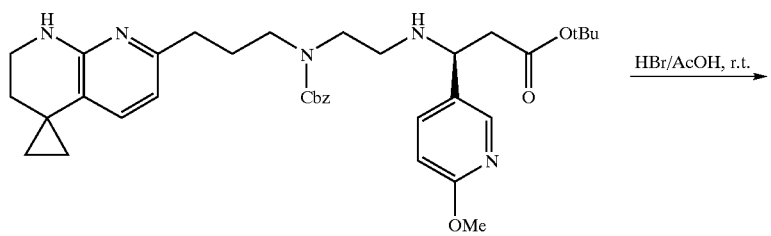

8-7

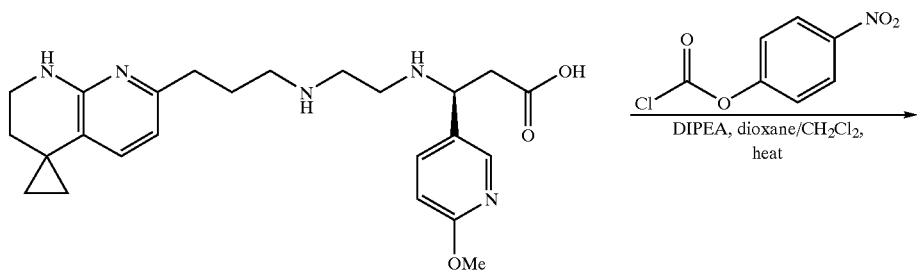

8-8

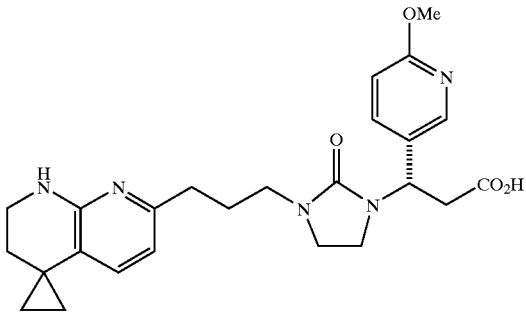

8-9

EXAMPLE 8

3(S)-(6-Methoxy-pyridin-3-yl)-3-{2-oxo-3-(5,6,7,8-tetrahydro-5,5-ethyleno-[1,8]naphthyridin-2-yl)-propyl]-imidazolidin-1-yl}-propionic acid (8-9)

1-Pyridin-3-yl-cyclopropanecarboxylic acid methyl ester (7-2)

To a cooled (−78° C.) solution of LDA (2.0M, 272 mL) in 500 mL anhydrous THF and 200 ml HMPA (dried with molecular sieves) was added gradually a solution of ethyl 3-pyridylacetate 7-1 (75.0 g, 454 mmol) in 50 mL THF. The mixture was stirred for 50 min at −78° C. and treated with neat 1,2-dibromoethane (117 mL, 1363 mmol) in one portion. The reaction mixture was stirred overnight while being allowed to warm to room temperature. The reaction mixture was quenched with saturated $NH_4Cl$ and extracted three times with EtOAc. The combined organic layers were washed three times with $H_2O$ and then brine. After solvent removal, the residue was purified using silica gel chromatography (100% hexanes to EtOAc/hexane=7/3) to obtain the desired product 7-2 as an oil.

$^1$H NMR (400 MHz, $CDCl_3$): δ 8.60 (m, 1H), 8.50 (m, 1H), 7.64 (m, 1H), 7.28 (m, 1H), 4.05 (q, 2H), 1.66 (q, 2H), 1.22 (q, 2H), 1.16 (t, 3H).

(1-Pyridin-3-yl-cyclopropyl)-methanol (7-3)

To a cooled (−78° C.) solution of 7-2 (76 g, 398 mmol) in 500 mL THF was added LiAlH$_4$ (1.0M, 250 mL, 250 mmol) gradually. The reaction mixture was stirred for 2 hr and quenched sequentially with 9.5 mL H$_2$O, 9.5 mL 15% NaOH, and 28.5 mL H$_2$O. The mixture was stirred overnight. Celite (50 g) was added and the mixture stirred for 20 min and filtered through a silica gel plug and concentrated to afford the desired product 7-3 as an oil which was used in the next step without further purification.

$^1$H NMR (400MHz, CDCl$_3$): δ 8.58 (m, 1H), 8.40 (m, 1H), 7.65 (m, 1H), 7.20 (m, 1H), 3.70 (s, 2H), 0.90 (m, 4H).

(1-Pyridin-3-yl-cyclopropyl)-acetonitrile (7-4)

To a cooled (−20° C.) solution of PPh$_3$ (2.6 g, 10 mmol) in 30 mL ether was added over 5 minutes a solution of DEAD (1.8 g, 10 mmol) in 20 mL ether. The mixture was stirred for 25 min at −20° C. A solution of 7-3 (1.0 g, 6.7 mmol) in 10 ml ether was added, and the reaction mixture was stirred for 30 min at −20° C. Acetone cyanohydrin (1.9 g, 20 mmol) was then added. The reaction mixture was stirred overnight while being allowed to warm to room temperature. After solvent removal, the residue was purified using silica gel chromatography (100% hexanes to 100% EtOAc) to obtain the desired product 724 as an oil.

$^1$H NMR (400MHz, CDCl$_3$): δ 8.65 (m, 1H), 8.54 (m, 1H), 7.72 (m, 1H), 7.29 (m, 1H), 2.68 (s, 2H), 1.06 (s, 4H).

2-(1-Pyridin-3-yl-cyclopropyl)-ethylamine (7-5)

To a cooled (0° C.) solution of 7-4 (31.3 g, 198 mmol) in 200 mL anhydrous THF was added borane-THF solution (1.5M, 660 mL, 990 mol). The reaction mixture was stirred at room temperature overnight. It was then quenched with methanol gradually until no gas was released. Then additional methanol (150 ml) was added, followed by 30 mL of 6N HCl. The mixture was stirred for 1 hr and concentrated to a viscous residue. It was then treated with 6N NaOH until pH >11 and stirred for 30 min and extracted four times with CHCl$_3$. After solvent removal, the residue was purified using silica gel chromatography (100%EtOAc to 50% EtOAc/46% EtOH/2% NH$_4$OH/2% H$_2$O) to obtain the desired product 7-5 as an oil.

Mass spectrum: Observed for [M+H]$^+$ 163.2; Calculated 162.12.

1,2,3,4-Tetrahydro-4,4-ethyleno-[1,8]naphthyridine (7-6)

To a mixture of 7-5 (15.0 g, 92.6 mmol) and 300 mL anhydrous toluene was added NaH (17.8 g, 445 mmol) gradually under nitrogen. The suspension was stirred at 120° C. for 8 hr. It was then cooled and quenched very slowly with EtOH until it became homogeneous. 150 mL of saturated NaHCO$_3$ was added. The mixture was extracted three times with EtOAc. The combined organic layers were washed with brine and dried (MgSO$_4$). After solvent removal, the residue was purified using silica gel chromatography (EtOAc/hexanes=1:2 to 100% EtOAc) to obtain the desired product 7-6 as an oil.

Mass spectrum: observed for [M+H]$^+$ 161.1; Calculated 160.12.

1,2,3,4-Tetrahydro-4,4-ethyleno-[1,8]naphthyridine-1-carboxylic acid tert-butyl ester (7-7)

A mixture of 7-6 (8.50 g, 53.1 mmol), di-tert-butyl dicarbonate (34.8 g, 159 mmol), and DMAP (0.13 g, 1.06 mmol) in 70 ml of 1,2-dichloroethane was heated at reflux for 5 hours, then cooled to room temperature, washed with saturated Na$_2$CO$_3$ solution, and brine separately. The solvents were removed under reduced pressure and the residue was purified by flash silica gel column chromatography (100% hexanes to 100% EtOAc) to provide 7-7 as a pale solid.

$^1$H NMR (400 MHz, CDCl$_3$): δ 8.28 (m, 1H), 6.95 (m, 2H), 3.91 (m, 2H), 1.81(m, 2H), 1.55 (s, 9H), 1.01 (m, 2H), 0.92(m, 2H).

8-Hydroxy-1,2,3,4-tetrahydro-4,4-ethyleno-[1,8] naphthyridine-1-carboxylic acid tert-butyl ester (7-8)

The mixture of 7-7 (5.85 g, 22.5 mmol) and 3-chloroperoxybenzoic acid (mCPBA) (6.11 g, 24.8 mmol) in 100 ml of CH$_2$Cl$_2$ was stirred at room temperature for three hours. The solvent was removed, the residue was diluted with water, and extracted with EtOAc. The combined organic extracts were washed with brine, dried with Na$_2$SO$_4$. After the solvent was removed, pure product 7-8 was obtained via flash silica gel column chromatography (100% EtOAc to 10% MeOH/90% EtOAc).

$^1$H NMR (400 MHz, CDCl$_3$): δ 7.98 (m, 1H), 6.86 (m, 1H), 6.50 (m, 1H), 3.95 (m, 1H), 3.61 (m, 1H), 1.75 (m, 2H), 1.44 (s, 9H), 1.03 (m, 2H), 0.95 (m, 2H).

8-Hydroxy-7-iodo-1,2,3,4-tetrahydro-4,4-ethyleno-[1,8] naphthyridine-1-carboxylic acid tert-butyl ester (7-9)

A solution of 7-8 (5.40 g, 19.5 mmol) in 50 ml of THF was added to a solution of LDA (2.0M in heptanes, THF, and ethylbenzene, 11.8 ml, 23.5 mmol) in 100 ml of THF at −78° C. under nitrogen. After the mixture was stirred at −78° C. for 1 hour, a solution of iodine (9.90 g, 39.0 mmol) in 50 ml of THF was added via cannula. The resulting mixture was stirred at −78° C. for 90 minutes, then quenched with AcOH (2.6 ml), warmed to room temperature and diluted with H$_2$O, NaHCO$_3$(aq), and Na$_2$S$_2$O$_3$ (aq). The mixture was extracted with EtOAc, the combined organic extracts were washed with brine, and dried with MgSO$_4$. After the solvent was removed, the product 7-9 was purified by flash silica gel column chromatography (20% EtOAc/80% hexanes to 65% EtOAc/35% hexanes).

$^1$H NMR (400 MHz, CDCl$_3$): δ 7.53 (d, 1H), 6.24 (d, 1H), 4.13 (m, 1H), 3.52 (m, 1H), 1.95 (m, 1H), 1.54 (m, 1H), 1.49 (s, 9H), 1.05 (m, 4H).

(Allyl-benzyloxycarbonyl-amino)-acetic acid tert-butyl ester (8-2)

To a mixture of 8-1 (6.30 g, 23.7 mmol) and allyl bromide (filtered through a short plug of poly(4-vinylpyridine) before use, 2.40 ml, 26.1 mmol) in 50 ml of THF and 50 ml of DMF at 0° C. under nitrogen was added NaH (60% dispersion in mineral oil, 1.05 g, 26.1 mmol) in one portion. The resulting mixture was stirred at 0° C. for 30 minutes, then at room temperature for three hours, quenched with saturated aqueous NH$_4$Cl solution, diluted with H$_2$O, and extracted with EtOAc. The combined organic extracts were washed with H$_2$O, brine, and dried with MgSO$_4$. After the solvent was removed, the product was purified by flash silica gel column chromatography (0% to 20% of EtOAc in hexanes).

$^1$H NMR (400 MHz, CDCl$_3$): δ 7.34(m, 5H), 5.80 (m, H), 5.16 (m, 4H), 4.00 (m, 2H), 3.87 (m, 2H), 1.41 (m, 9H).

Allyl-[(methoxy-methyl-carbamoyl)-methyl]-carbamic acid benzyl ester (8-3)

A mixture of 8-2 (6.0 g, 19.6 mmol) and 10 ml of TFA was stirred at 60° C. for 20 minutes. The volatiles were removed under reduced pressure, the residue was azeotroped with toluene (20 ml×3), then dissolved in 60 ml of anhydrous DMF, and to which was added N,O-dimethylhydroxylamine hydrochloride (2.20 g, 21.7 mmol), DIPEA (10.3 ml, 59.1 mmol), and TBTU (6.97 g, 21.7 mmol) at room temperature. The resulting mixture was stirred for 1.5 hr, diluted with H$_2$O, and extracted with EtOAc. The organic layer was then washed with saturated aqueous Na$_2$CO$_3$ solution, H$_2$O, and brine separately, and then dried with MgSO$_4$. After the solvent was removed, the product was purified by flash silica gel column chromatography (0% to 45% of EtOAc in hexanes).

¹H NMR (400 MHz, CDCl₃): δ 7.34(m, 5H), 5.81 (m, H), 5.17(m, 4H), 4.10 (m, 4H), 3.73/3.54 (s, 3H), 3.20/3.15 (s, 3H).

1-Hydroxy-2-(3-{benzyloxycarbonyl-[(methoxy-methyl-carbamoyl)-methyl]-amino}-propyl)-8-tert-butoxycarbonyl-5,6,7,8-tetrahydro-5,5-ethyleno-1,8] naphthyridine (8-4)

A mixture of 8-3 (4.1 g, 14.0 mmol) and 9-BBN (0.5M solution in THF, 34.0 ml, 16.8 mmol) was stirred at room temperature under nitrogen for 15 hours. The volatiles were removed under reduced pressure, the residue was dissolved in 150 ml of DMF, and to which was added 7-9 (5.55 g, 13.8 mmol), K₂CO₃ (2.90 g, 21.0 mmol), Pd(OAc)₂(0.31 g, 1.40 mmol), and DPPF (0.78 g, 1.40 mmol). The resulting mixture was then stirred at 60° C. for 1 hour, at 110° C. for 30 minutes, cooled to room temperature, diluted with H₂O, and extracted with EtOAc. The combined organic extracts were washed with H₂O, brine, and dried with MgSO₄. After the solvents were removed, the product was purified by flash silica gel column chromatography (0% to 80% of EtOAc/MeOH(8:2) in hexanes).

¹H NMR (400 MHz, CDCl₃): δ 7.34 (m, 5H), 5.81 (m, H), 5.17 (m, 4H), 4.10 (m, 4H), 3.73/3.54 (s, 3H), 3.20/3.15 (s, 3H). MS: [M+H]⁺=569.1

1-Hydroxy-2-[3-(benzyloxycarbonyl-{2-[1-(6-methoxy-pyridin-3-yl)-3-oxo-butylamino]-ethyl}-amino)-propyl)]-8-tert-butoxycarbonyl-5,6,7,8-tetrahydro-5,5-ethyleno-[1,8] naphthyridine (8-6).

DIBAL-H (1.0M solution in hexanes, 8.80 ml, 8.80 mmol) was added dropwise to a stirred solution of 8-4 (2.00 g, 3.52 mmol) in 40 ml of anhydrous THF at −78° C. After 2 hours, the mixture was warmed to room temperature and quenched by slow addition of MeOH (1.6 ml). A 1.0M aqueous Rochelle salt solution was added, and the mixture was stirred for 30 minutes. EtOAc was added, the organic layer was separated and dried with MgSO₄, the solvent was removed under reduced pressure, and the crude product 8-5 was azeotroped with toluene, then dissolved in 40 ml of isopropanol. To the solution was added 3(S)-(6-methoxypyridin-3-yl)-β-alanine tert-butyl ester p-toluenesulfonic acid salt 1-5 (1.73 g, 4.22 mmol), NaOAc (2.89 g, 35.2 mmol), and 3.5 g of powdered molecular sieves. The mixture was stirred at room temperature for 12 hours and was cooled to 0° C., and NaCNBH₃ (0.67 g, 10.6 mmol) was added in one portion. The mixture was then warmed to room temperature and stirred for 24 hours. 1H HCl was added to bring the pH to 2. After the mixture was stirred for 10 minutes, EtOAc was added, the pH was then adjusted to 11 with saturated aqueous Na₂CO₃. The organic portion was separated and dried with MgSO₄, filtered, concentrated, and purified by flash silica gel column chromatography (0% to 10% of MeOH in EtOAc).

Mass spectrum: Observed [M+H]⁺=746.3.

3-(2-{Benzyloxycarbonyl-[3-(5,6,7,8-tetrahdro-5,5-ethyleno-[1,8]naphthyridin-2-yl)-propyl]-amino}-ethylamino)-3(S)-(6-methoxypyridin-3-yl)-propionic acid tert-butyl ester (8-7)

Zinc powder (100 mesh, 2.0 g, 30.2 mmol) was added in one portion to the solution of 8-6 (1.50 g, 2.01 mmol) in 12 ml of AcOH and 2 ml of H₂O at 70° C. The mixture was then stirred at 70° C. for 30 minutes and then cooled to room temperature. The solids were removed by filtration, the solvents were removed under reduced pressure, and the residue was partitioned between EtOAc and 5% aqueous NH₄OH. The organic layer was then washed with brine and dried with MgSO₄. The solvent was removed to afford the crude product which was used in the preparation of 8-8 without further purification.

Mass spectrum: observed [M+H]⁺=630.2.

3(S)-(6-Methoxy-pyridin-3-yl)-3-{2-[3-(5,6,7,8-tetrahydro-5,5-ethyleno-[1,8]naphthyridin-2-yl)-propylamino]-ethylamino}-propionic acid (8-8)

Crude 8-7 (2.01 mmol) in 3 ml of HBr (30 wt. % solution in AcOH) and 3 ml of AcOH was stirred at room temperature for 30 minutes, ether was added, the mixture was stirred for 10 minutes, the ether solution was removed by decantation, the residue was purified by flash silica gel column chromatography (5% to 20% of MeOH in CH₂Cl₂ with 4% of NH₄OH) to afford the title compound.

Mass spectrum: observed [M+H]⁺=440.2.

3(S)-(6-Methoxy-pyridin-3-yl)-3-{2-oxo-3-(5,6,7,8-tetrahydro-5,5-ethyleno-[1,8]naphthyridin-2-yl)-propyl]-imidazolidin-1-yl}-propionic acid (8-9)

A solution of 4-nitrophenyl chloroformate (0.29 g, 1.46 mmol) in 20 ml of 1,4-dioxane was added dropwise to a mixture of 8-8 (0.61 g, 1.39 mmol) and DIPEA (1.1 ml, 6.26 mmol) in 150 ml of 1,4-dioxane and 60 ml of CH₂Cl₂ at 0° C. under nitrogen. The resulting mixture was stirred at 0° C. for 40 minutes, warmed to room temperature, then heated at reflux for three hours. The volatiles were removed under reduced pressure and the product was purified by flash silica gel column chromatography (5% to 15% of MeOH in CH₂Cl₂ with 3% of NH₄OH).

¹H NMR (400 MHz): δ 11.0 (s, broad, 1H), 8.11 (m, 1H), 7.57 (m, 1H), 6.91 (d, 1H), 6.72( d, 1H), 6.28 (d, 1H), 5.57 (m, 1H), 3.92 (s, 3H), 3.38-3.66 (m, 5H), 3.16 (q, 1H), 2.95-3.03 (m, 2H), 2.65-2.85 (m, 4H), 1.90-1.98 (m, 1H), 1.74-1.83 (m, 1H), 1.69 (t, 2H), 1.01 (m, 2H), 0.83 (m, 2H).

Mass spectrum: [M+H]⁺=466.2.

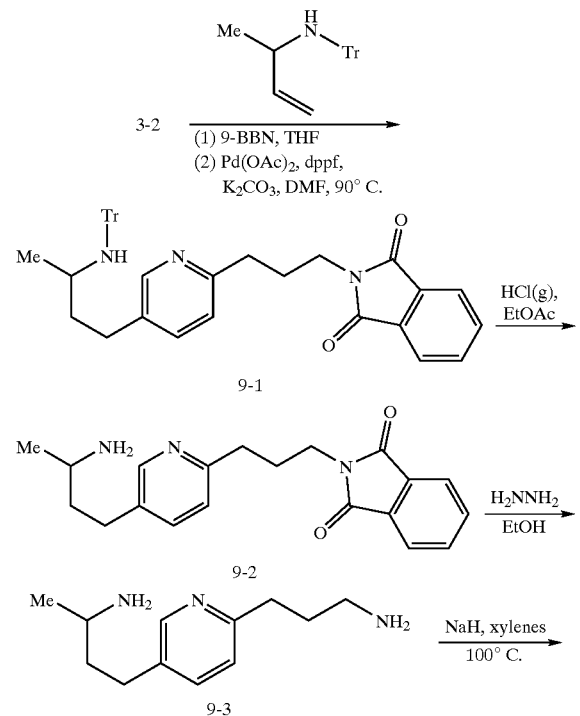

Scheme 9

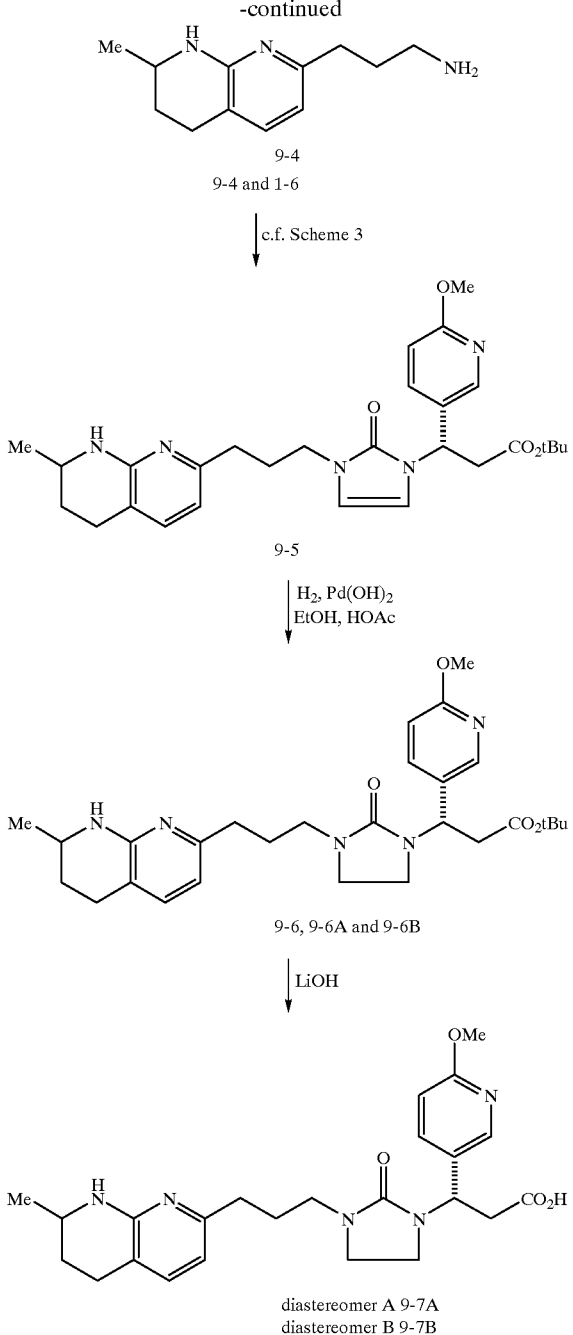

3(S)-(6-Methoxy-pyridin-3-yl)-3-{2-oxo-3-(7-methyl-5,6,7,8-tetrahydro-[1,8]naphthyridin-2-yl)-propyl]-imidazolidin-1-yl}-propionic acid (9-7A and 9-7B)

Step A: 2-[3-(5-(3-N-tritylaminobut-1-yl)-pyridin-2-yl)-propyl]-isoindole-1,3-dione (9-1)

3-Tritylaminobut-1-ene (A. Albeck and R. Persky, *J. Org. Chem.*, 1994, 59, 653; 5.75 g, 18.4 mmol) was added to a solution of 9-BBN (44 mL of 0.5M in THF, 22 mmol) and the mixture stirred for 18 hours at ambient temperature. $K_2CO_3$ (3.8 g, 28 mmol), bromopyridine 3-2 (6.34 g, 18 mmol), $Pd(OAc)_2$ (4.12 mg, 1.84 mmol), DPPF (1.02 g, 1.84 mmol) and DMF (50 mL) were added and the mixture degassed with nitrogen gas. The resulting mixture was stirred for 18 hours at 90° C., cooled, concentrated in vacuo to 50 mL and then treated with ethyl acetate (100 mL), saturated $Na_2CO_3$ (75 mL) and $NaBO_3.4H_2O$ (40 g). The mixture was stirred for 3 hours, partitioned between EtOAc and water, extracted with EtOAc, washed with water and brine, dried over $MgSO_4$, and concentrated. The residue was chromatographed on silica gel (33% EtOAc/hexane) to give 9-1.

$^1$H NMR (500 MHz, $CDCl_3$) δ 8.12 (s, 1H), 7.83 (m, 2H), 7.70 (m, 2H), 7.55 (m, 6H), 7.49 (d, 1H), 7.2 (m, 9H), 7.02 (d, 1H), 4.12 (dq, 1H), 3.77 (dt, 2H), 2.80 (m, 2H), 2.6 (m, 1H), 2.43 (m, 1H), 2.22 (m, 1H), 2.12 (m, 2H), 1.27 (m, 2H), 0.82 (dd, 3H).

Step B: 2-[3-(5-(3-aminobut-1-yl)-pyridin-2-yl)-propyl]-isoindole-1,3-dione (9-2)

A solution of the tritylamine 9-1 (6.75 g, 11.7 mmol) in EtOAc (150 mL) was treated with HCl gas until saturated. After 30 minutes the mixture was extracted with 1N HCl (5×) then the aqueous solution was basified with solid $K_2CO_3$ and extracted with EtOAc (3×). The organic layers were washed with water then brine, dried ($MgSO_4$) and concentrated in vacuo to give the title compound 9-2 as an oil which was used in Step C without further purification.
Mass spectrum: M+H found 338.8. Calculated 338.2.

Step C: 3-(5-(3-aminobut-1-yl)-pyridin-2-yl)-propylamine (9-3)

A solution of the phthalimide 9-2 (3.05 g, 9.05 mmol) in EtOH (50 mL) was treated with hydrazine (2.84 mL, 90.5 mmol) and heated to 500C for 1 hour. The mixture was cooled, methyl t-butylether (100 mL) added, stirred for 1 hour and filtered. The filtrate was concentrated in vacuo to give the desired product 9-3 which was used in Step D without further purification.
Mass spectrum: M+H found 208.2. Calculated 208.2.

Step D: 3-(7-methyl-5,6,7,8-tetrahydro [1,8]naphthyridin-2-yl)-propylamine (9-4)

A solution of the diamine 9-3 (1.87 g, 9.05 mmol) in xylenes (100 mL) was degassed with nitrogen gas then treated with NaH (1.3 g, 54.3 mmol) and then heated to 100° C. for 16 hours. Mass spectrum indicated desired product formed. The mixture was cooled, EtOH added then poured into water and extracted with EtOAc. The organic layer was washed with water, brine dried ($MgSO_4$) and concentrated. Purification of the residue on silica gel (2%-5% MeOH/$CHCl_3$) gave a solid which was shown to be the N-acetate of the desired compound by mass spectrum and nm. Treatment with aqueous NaOH/THF/MeOH at reflux for 72 hours then afforded the hydrolysed product. The THF/MeOH was removed in vacuo, the residue was partitioned between water and $CH_2Cl_2$, washed with brine and dried over $MgSO_4$. Removal of the solvent afforded the title compound 9-4.
Mass spectrum: M+H found 206.2. Calculated 206.2

Step E: 3(S)-(6-Methoxy-pyridin-3-yl)-3-{2-oxo-3-(7-methyl -5,6,7,8-tetrahydro -[1,8]naphthyridin-2-yl)-propyl]-2,3-dihydro-imidazol-1-yl}-propionic acid tert-butyl ester (9-5)

Following the procedure described for Scheme 3, the amine 9-4 and dimethoxyacetal 1-6 were converted to the title compound 9-5.
Mass spectrum: M+H found 508.1. Calculated 508.3.

Step F: 3(S)-(6-Methoxy-pyridin-3-yl)-3-{2-oxo-3-(7-methyl -5,6,7,8-tetrahydro -[1,8]naphthyridin-2-yl)-propyl]-imidazolidin-1-yl}-propionic acid tert-butyl ester (9-6, 9-6A and 9-6B).

A solution of the ester 9-5 (700 mg, 1.38 mmol) in EtOH (50 mL) and HOAc (1 mL) was degassed with nitrogen gas then treated with $Pd(OH)_2$ on carbon and then placed on a Parr hydrogenation apparatus. The mixture was hydrogenated using 70 psi hydrogen gas for 16 hours. After filtration, the solvent was removed in vacuo to give the title compound 9-6 as a 1:1 mixture of methyl diastereomers.
Mass spectrum: M+H found 510.2. Calculated 510.3.
Preparative HPLC using Chiracel AD column eluted with 30:70 hexane:EtOAc (with 0.1%diethylamine) afforded pure diastereomer A (9-6A) as the faster eluting component. Continued elution afforded the slower eluting diastereomer B (9-6B).
Step G: 3(S)-(6-Methoxy-pyridin-3-yl)-3-{2-oxo-3-(7-methyl -5,6,7,8-tetrahydro-[1,8]naphthyridin-2-yl)-propyl]-imidazolidin-1-yl}-propionic acid (9-7A and 9-7B)

A solution of the ester 9-6A (200 mg, 0.39 mmol) in MeOH (20 mL), THF (20 mL), water (20 mL) and 1N LiOH (50 mL) was heated at 60° C. for 48 hours. The mixture was concentrated and purified by reverse phase HPLC (C-18 column; 5:95 $CH_3CN:H_2O$ with 0.1% TFA; gradient) to give, after lyophilization, the title compound 9-7A as a TFA salt.
High resolution mass spectrum: found 454.2447. M+H calculated for $C_{24}H_{32}N_5O_4$ 454.2449.
$^1$H NMR (500 MHz, $CD_3OD$): δ 8.13 (d, 1H), 7.73 (dd, 1H), 7.59 (d, 1H), 6.82 (d, 1H), 6.64 (d, 1H), 5.41 (t, 1H), 3.90 (s, 3H), 3.72 (m, 1H), 3.48 (m, 1H), 3.39 (m, 2H), 3.24 (m, 2H), 3.11 (m, 1H), 3.03 (m, 2H), 2.83 (m, 2H), 2.68 (t, 2H), 2.05 (m, 1H), 1.87 (m, 2H), 1.63 (m, 1H), 1.34 (d, 3H).
Following the procedure described above, the ester 9-6B was converted into the acid 9-7B.
High resolution mass spectrum: found 454.2449. M+H calculated for $C_{24}H_{32}N_5O_4$ 454.2449.
$^1$H NMR (500 MHz, $CD_3OD$) δ 8.14 (d, 1H), 7.74 (dd, 1H), 7.59 (d, 1H), 6.83 (d, 1H), 6.64 (d, 1H), 5.41 (t, 1H), 3.91 (s, 3H), 3.74 (m, 1H), 3.49 (m, 1H), 3.39 (m, 2H), 3.24 (m, 2H), 3.11 (m, 1H), 3.04 (m, 2H), 2.84 (m, 2H), 2.67 (t, 2H), 2.05 (m, 1H), 1.87 (m, 2H), 1.63 (m, 1H), 1.34 (d, 3H).

The following compounds whose structures are depicted below can also be prepared as described above and depicted in Schemes 1–8 using synthetic methodologies or variations thereon which are known and understood by those skilled in the art of synthetic organic chemistry:

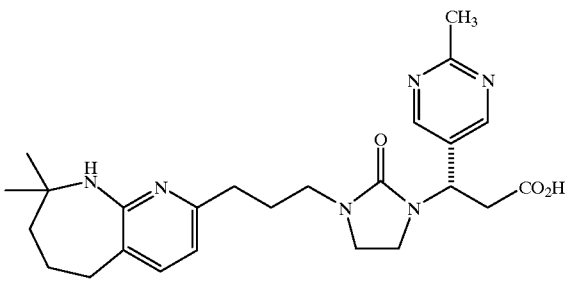

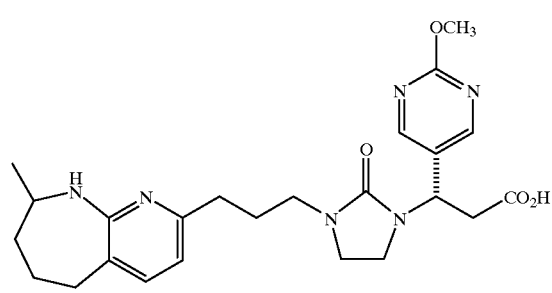

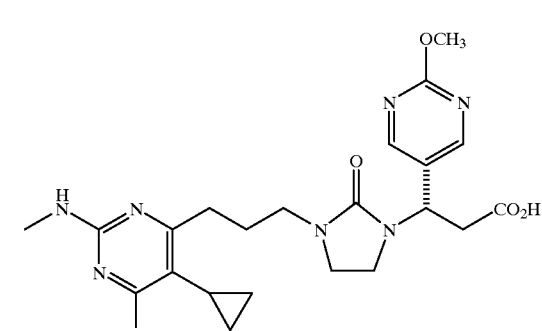

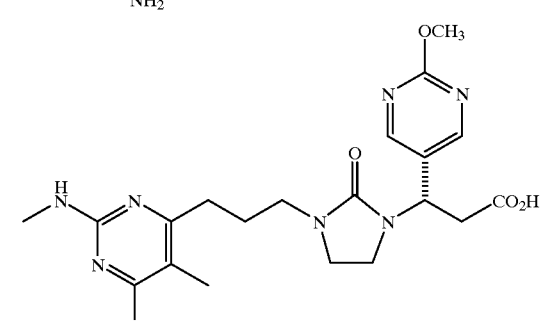

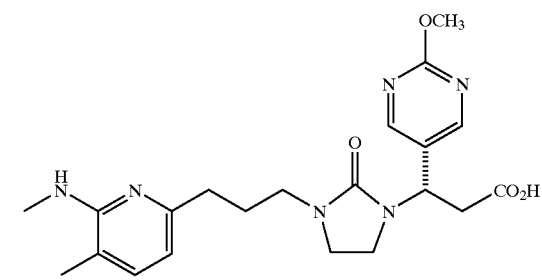

-continued
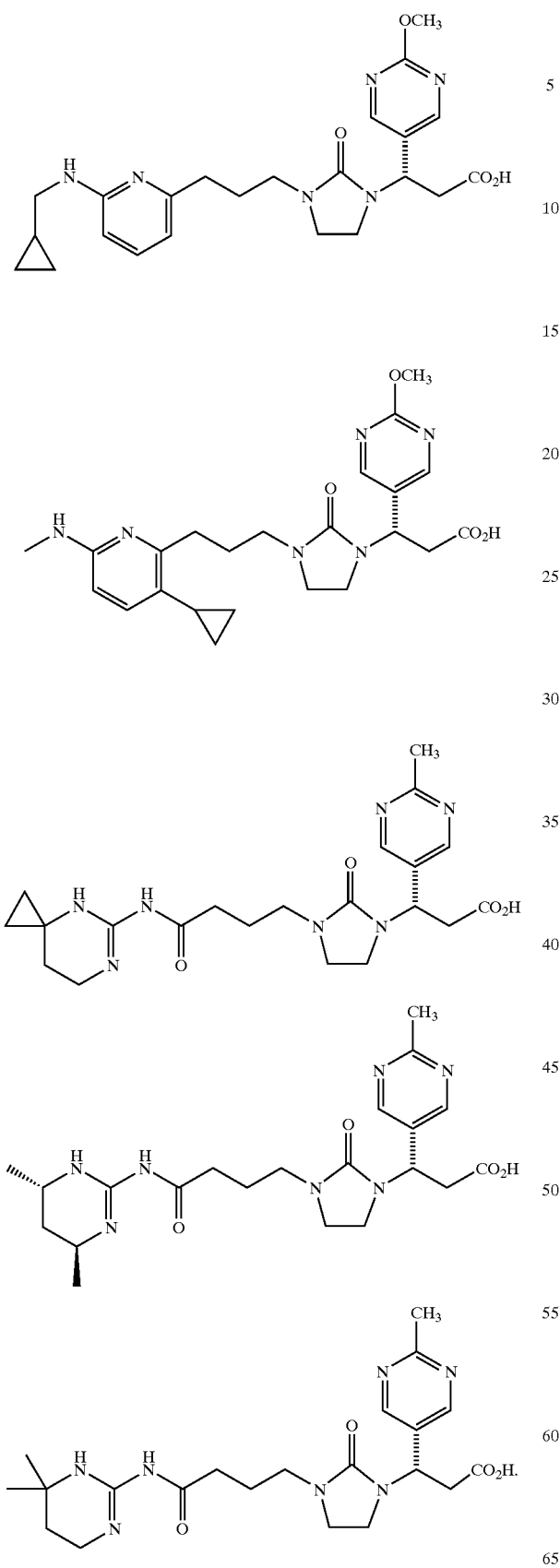
SCHEME A
Synthesis of Radioligand for SPAV3 Assay
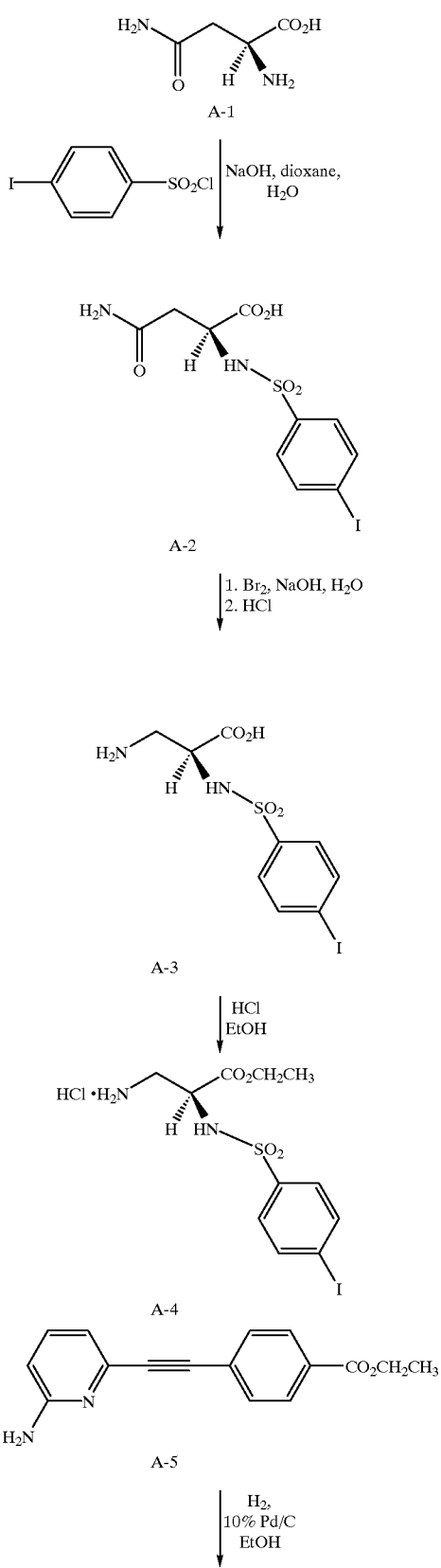

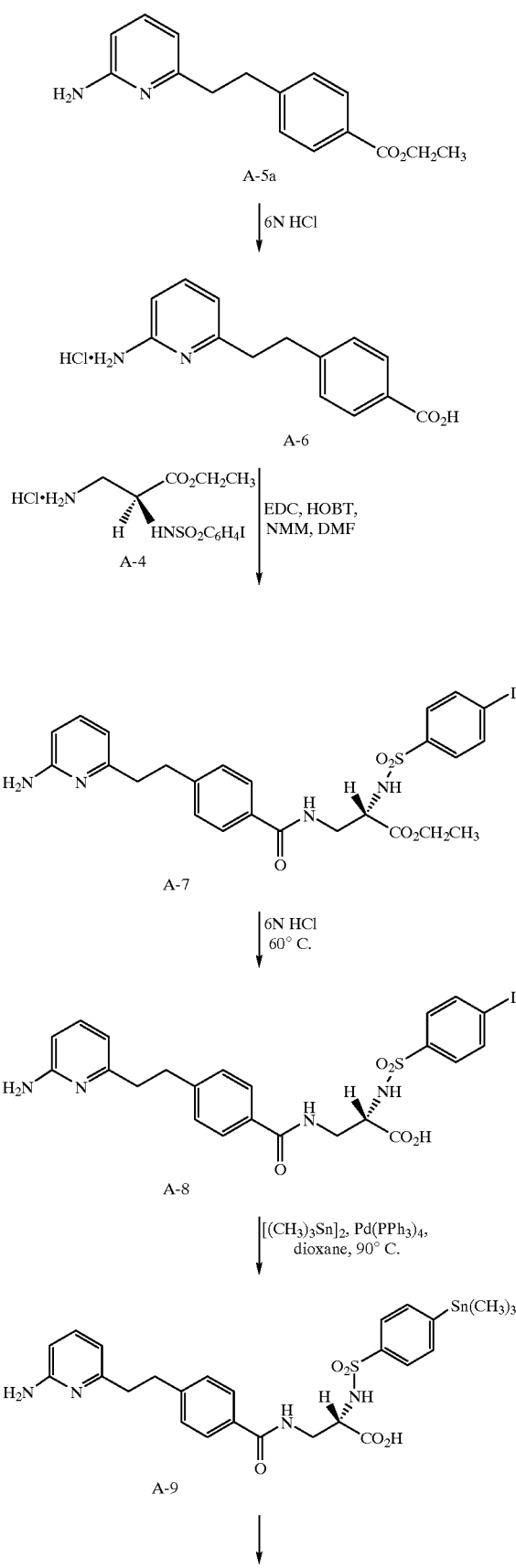

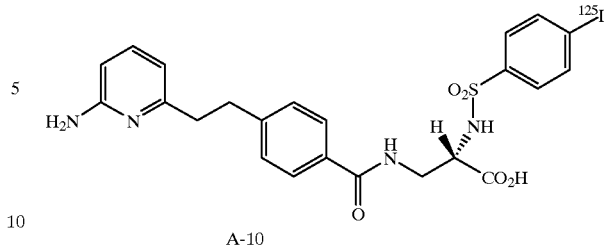

N-(4-iodo-phenylsulfonylamino)-L-asparagine (A-2)

To a stirred solution of acid A-1 (4.39 g, 33.2 mmol), NaOH (1.49 g, 37.2 mmol), dioxane (30 ml) and H$_2$O (30 ml) at 0° C. was added pipsyl chloride (10.34 g, 34.2 mmol). After 5 minutes, NaOH (1.49, 37.2 mmol) dissolved in 15 ml H$_2$O, was added followed by the removal of the cooling bath. After 2.0 h, the reaction mixture was concentrated. The residue was dissolved in H$_2$O (300 ml) and then washed with EtOAc. The aqueous portion was cooled to 0° C. and then acidified with concentrated HCl. The solid was collected and then washed with Et$_2$O to provide acid A-2 as a white solid.
$^1$H NMR (300 MHz, D$_2$O) δ 7.86 (d, 2H, J=8 Hz ), 7.48 (d, 2H, J=8 Hz) 3.70 (m, 1H), 2.39 (m, 2H).

2(S)-(4-Iodo-phenylsulfonylamino)-β-alanine (A-3)

To a stirred solution of NaOH (7.14 g, 181.8 mmol) and H$_2$O (40 ml) at 0° C. was added Br$_2$ (1.30 ml, 24.9 mmol) dropwise over a ten minute period. After ~5 minutes, acid A-2 (9.9 g, 24.9 mmol), NaOH (2.00 g, 49.8 mmol) and H$_2$O (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.
$^1$H NMR (300 MHz, D$_2$O) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S )-(4-iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.
$^1$H NMR (300 MHz, CD$_3$OD) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (A-5a)

A mixture of ester A5 (700 mg, 2.63 mmol), (for preparation, see: Scheme 29 (intermediate 29-3) of U.S. Pat. No. 5,741,796 (Apr. 21, 1998)), 10% Pd/C (350 mg) and EtOH were stirred under 1 atm H$_2$. After 20 h, the reaction was filtered through a celite pad and then concentrated to provide ester A-5a as a brown oil.
TLC R$_f$=0.23 (silica, 40% EtOAc/hexanes)
$^1$H NMR (300 MHz, CDCl$_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (A-6)

A suspension of ester A-5a (625 mg, 2.31 mmol) in 6N HCl (12 ml) was heated to 60° C. After 20 h, the reaction was concentrated to give acid A-6 as a tan solid.

¹H NMR (300 MHz, CD₃OD) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodo-phenylsulfonylamino-β-alanine (A-7)

A solution of acid 15-6 (400 mg, 1.43 mmol), amine A (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. NaHCO₃, brine, dried (MgSO₄) and concentrated. Flash chromatography (silica, EtOAc then 5% isopropanol/EtOAc) provided amide A-7 as a white solid.

TLC R$_f$=0.4 (silica, 10% isopropanol/EtOAc)
¹H NMR (300 MHz, CD₃OD) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenyl-sulfonylamino)-β-alanine (A-8)

A solution of ester A-7 (200 mg, 0.3213 mmol) and 6N HCl (30 ml) was heated to 60° C. After 20 h, the reaction mixture was concentrated. Flash chromatography (silica, 20:20:1:1 EtOAc/EtOH/ NH₄OH/H₂O) provided acid A-8 as a white solid.

TLC R$_f$=0.45 (silica, 20:20:1:1 EtOAc/EtOH/NH₄OH/H₂O)
¹H NMR (400 MHz, DMSO-d₆) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethylbenzoyl-2(S)-(4-trimethylstannyl-phenylsulfonylamino-β-alanine (A-9)

A solution of iodide A-8 (70 mg, 0.1178 mmol), [(CH₃)₃Sn]₂ (49 μl, 0.2356 mmol), Pd(PPh₃)₄ (5 mg) and dioxane (7 ml) was heated to 90° C. After 2 h, the reaction was concentrated and then purified by preparative HPLC (Delta-Pak C₁₈ 15 μM 100A°, 40×100 mm; 95:5 then 5:95 H₂O/CH₃CN) to provide the trifluoroacetate salt. The salt was suspended in H₂O (10 ml), treated with NH₄OH (5 drops) and then lyophilized to provide amide A-9 as a white solid.
¹H NMR (400 MHz, DMSO-d₆) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95-7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodo-phenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% H₂SO₄/MeOH was made and immediately added to the Na$^{125}$I/iodobead vial. After stirring for three minutes at room temperature, approximately 0.04–0.05 mL of NH₄OH was added so the reaction mixture was at pH 6-7. The entire reaction mixture was injected onto the HPLC for purification [Vydac peptide-protein C-18 column, 4.6×250 mm, linear gradient of 10% acetonitrile (0.1% (TFA):H₂O (0.1% TFA) to 90% acetonitrile (0.1% TFA):H₂O (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

SCHEME B
Synthesis of Radioligand for SPAV5 Assay

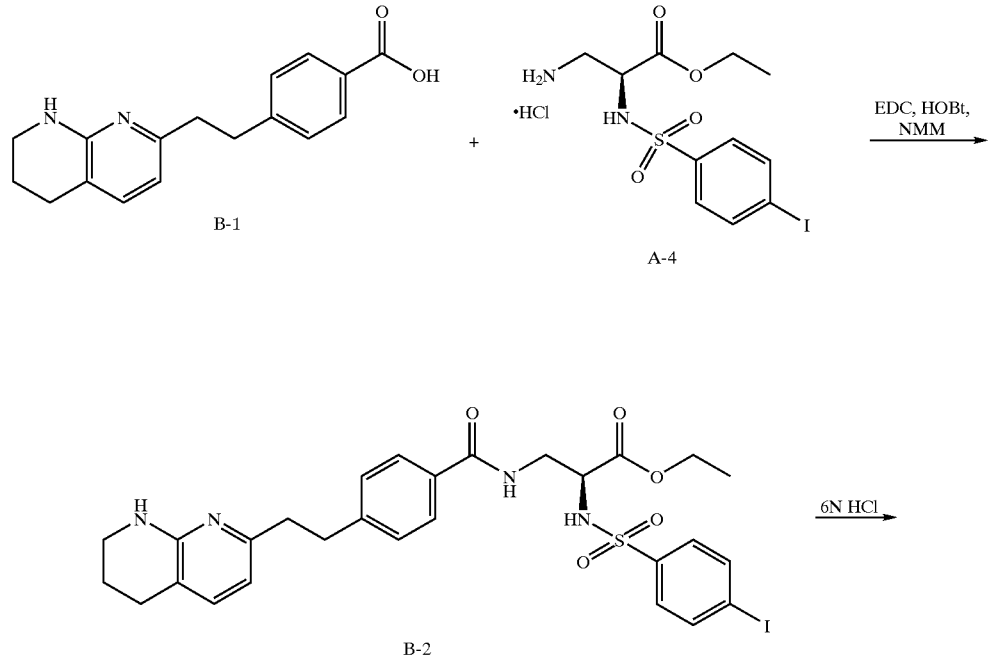

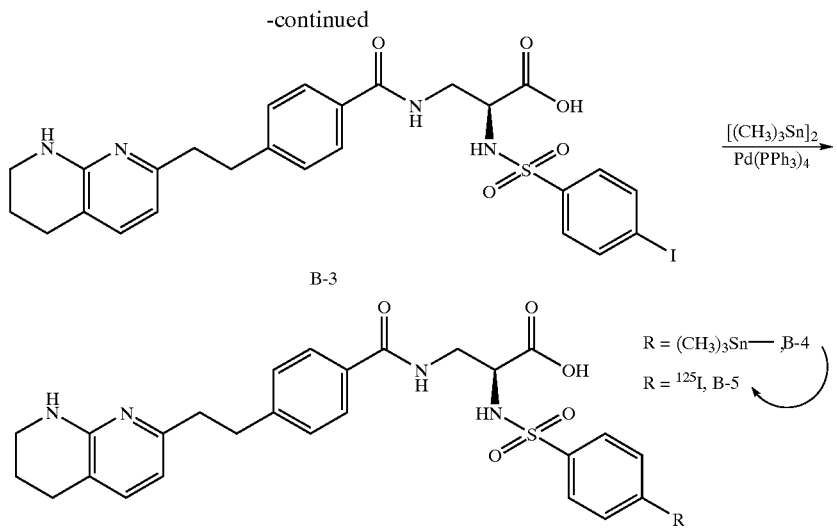

B-3

R = (CH₃)₃Sn — B-4
R = ¹²⁵I, B-5

2(S)-(4-Iodo-benzenesulfonylamino)-3-{4-[2-(5,6,7,8-tetrahydro-[1,8]naphthyridin-2-yl)-ethyl]-benzoylamino}-propionic acid ethyl ester (B-2)

A mixture of B-1I (0.23 g, 0.72 mmol; for preparation see U.S. Pat. No. 5,741,796), A-4 (0.343 g, 0.792 mmol), EDC (0.179 g, 0.93 mmol), HOBT (0.126 g, 0.93 mmol), NMM (0.316 mL, 2.86 mmol) in acetonitrile (3 mL) and DMF (3 mL) was stirred for 2 hours at ambient temperature then diluted with ethyl acetate, washed with water, saturated aqueous NaHCO₃, and brine, dried over MgSO₄, and concentrated. The residue was chromatographed on silica gel (70:25:5 CHCl₃/EtOAc/MeOH) to give B-2 as a white solid. TLC $R_f$=0.22 (silica, 70:25:5 CHCl₃/EtOAc/MeOH).
¹H NMR (300 MHz, CDCl₃) δ 7.79 (d, 2H, J=8 Hz), 7.63 (d, 2H, J=8 Hz), 7.54 (d, 2H, J=8 Hz), 7.27 (d, 2H, J=8 Hz),7.04 (d, 1H, J=7 Hz), 6.60 (m, 1H), 6.29 (d, 1H, J=7 Hz), 4.83 (br s, 1H), 4.09 (m, 3H), 3.84 (m, 1H), 3.68 (m, 1H), 3.42 (m, 2H), 3.01 (m, 4H), 2.86 (m, 4H), 2.69 (t, 2H, J=6 Hz), 1.88 (m, 2H).

2(S)-(4-Iodo-benzenesulfonylamino)-3-{4-[2-(5,6,7,8-tetrahydro-[1,8]naphthyridin-2-yl)-ethyl]-benzoylamino}-propionic acid (B-3)

A mixture of B-2 (0.38 g, 0.573 mmol) and 6N HCl (50 mL) was stirred for 14 hours at 60° C. After cooling to room temperature, the mixture was concentrated, and the residue chromatographed on silica gel (25:10:1:1 to 15:10:1:1 EtOAc/EtOH/NH₄OH/H₂O) to give B-3 as a white solid. TLC $R_f$=0.43 (silica, 10:10:1:1 EtOAc/EtOH/NH₄OH/H₂O).
¹H NMR (300 MHz, DMSO-d₆) δ 8.42 (m, 1H), 7.79 (d, 2H, J=8 Hz), 7.63 (d, 2H, J=8 Hz), 7.44 (d, 2H, J=8 Hz), 7.27 (d, 2H, J=8 Hz),7.10 (d, 1H, J=7 Hz), 6.58 (br s, 1H), 6.32 (d, 1H, J=7 Hz), 3.96 (m, 1H), 3.51 (m, 1H), 3.30 (m, 5H), 2.96 (m, 2H), 2.78 (m, 2H), 2.62 (m, 2H), 1.77 (m, 2H).
HRMS: For C₂₆H₂₇IN₄O₅S, expected 635.0818, found 635.0831.

3-{4-[2-(5,6,7,8-Tetrahydro-[1,8]naphthyridin-2-yl)-ethyl]-benzoylamino}-2(S)-(4-trimethylstannanyl-benzenesulfonylamino)-propionic acid (B-4)

A mixture of B-3 (0.10 g, 0.16 mmol), hexamethyldistannane (0.065 mL, 0.32 mmol), Pd(PPh₃)₄, and dioxane (10 mL) was stirred for one hour at 90° C. After cooling to room temperature, the mixture was concentrated, and the residue chromatographed on silica gel (50:10:1:1 to 25:10:1:1 EtOAc/EtOH/NH₄OH/H₂O) to give B-4 as a white solid.

TLC $R_f$=0.48 (silica, 15:10:1:1 EtOAc/EtOH/NH₄OH/H₂O).
¹H NMR (300 MHz, DMSO-d₆) δ 8.38 (m, 1H), 8.14 (m, 1H), 7.63 (m, 4H), 7.28 (d, 2H, J=8 Hz), 7.08 (d, 1H, J=7 Hz), 6.50 (br s, 1H), 6.28 (d, 1H, J=7 Hz), 3.96 (m, 1H), 3.48 (m, 1H), 3.31 (m, 5H), 2.96 (m, 2H), 2.78 (m, 2H), 2.62 (m, 2H), 1.77 (m, 2H), 0.28 (s, 9H).
High resolution mass spectrum: For C₂₉H₃₆N₄O₅SSn, expected 665.1533 (¹¹²Sn) and 673.1507 (¹²⁰Sn), found 665.1510 and 673.1505.

2(S)-(4-¹²⁵Iodo-benzenesulfonylamino)-3-[4-[2-(5,6,7 8-tetrahydro-[1,8]naphthyridin-2-yl)-ethyl]-benzoylaamino}-propionic acid (B-5)

A stir bar, methanol (0.05 mL) and an iodobead (Pierce) were added to a shipping vial of Na¹²⁵I (10 mCi, Amersham, IMS300) and stirred for five minutes at room temperature. A solution of B-4 (~0.1 mg) in methanol (0.04 mL) was made and a portion (0.02 mL) was added to a mixture of H₂SO₄ (0.005 mL) in methanol (0.025 mL), and this solution was added immediately to the Na¹²⁵I/iodobead vial. After stirring for two minutes at room temperature, the reaction was quenched with NH₄OH (0.04–0.05 mL) and the entire reaction mixture was injected onto the BPLC for purification [Vydac peptide-protein C-18 column, 4.6×250 mm, linear gradient of 10% acetonitrile :H₂O (0.1% TFA) to 90% acetonitrile:H₂O (0.1% TFA) over 20 minutes, 1 mL/min]. The retention time of B-5 is 16 minutes under these conditions. Fractions containing the majority of the radioactivity were pooled, lyophilized and diluted with ethanol to give approximately 1 mCi of B-5, which coeluted on HPLC analysis with an authentic sample of B-3.

Instrumentation: Analytical and preparative BPLC was carried out using a Waters 600E Powerline Multi Solvent Delivery System with 0.1 mL heads with a Rheodyne 7125 injector and a Waters 990 Photodiode Array Detector with a Gilson FC₂₀₃ Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UVNvis Diode Array Spectrophotometer. Sample radioactivities were determined in a Packard A5530 gamma counter.

The test procedures employed to measure αvβ3 and αvβ5 binding and the bone resorption inhibiting activity of the compounds of the present invention are described below.

BONE RESORPTION-PIT ASSAY

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, Ill.). Bone slices are pooled, placed in a 10% ethanol solution and refrigerated until further use.

Prior to experimentation, bovine bone slices are ultrasonicated twice, minutes each in $H_2O$. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml αMEM, pH 6.9 containing 5% fetal bovine serum and 1% penicillin/streptomycin.

Long bones from 7–14 day old rabbits (New Zealand White Hare) are dissected, cleaned of soft tissue and placed in αMEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~$2\times10^7$ cells/ml). A cell suspension consisting of $5\times10^6$/ml in αMEM containing 5% fetal bovine serum, 10 nM $1,25(OH)_2D_3$, and penicillin-streptomycin is prepared. 200 ml aliquots are added to bovine bone slices (200 mm×6 mm) and incubated for 2 hrs. at 37° C. in a humidified 5% $CO_2$ atmosphere. The medium is removed gently with a micropipettor and fresh medium containing test compounds is added. The cultures are incubated for 48 hrs., and assayed for c-telopeptide (fragments of the al chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of $H_2O$, and the bone slices are then fixed for 20 minutes in 2.5% glutaraldehyde, 0.1M cacodylate, pH 7.4. After fixation, any remaining cellular debris is removed by 2 min. ultrasonication in the presence of 0.25M $NH_4OH$ followed by 2×15 min ultrasonication in $H_2O$. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting $IC_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp. 31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8: S378 (1993), describes a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture 1. 175 μl TBS buffer (50 mM Tris.HCl pH 7.2, 150 mM NaCl, 1% BSA, 1 mM $CaCl_2$, 1 mM $MgCl_2$).
2. 25 ml cell extract (dilute with 100 mM octylglucoside buffer to give 2000 cpm/25 μl ).
3. $^{125}I$-echistatin (25 μl/150,000 cpm) (see EP 382 451).
4. 25 μl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% poly-ethyleneimine for 10 mins) were then washed with the wash buffer (50 mM Tris HCl, 1 mM $CaCl_2/MgCl_2$, pH 7.2). The filter was then counted in a gamma counter.

SPAV3 ASSAY

MATERIALS

1. Wheat germ agglutinin Scintillation Proximity Beads (SPA): Amersham
2. Octylglucopyranoside: Calbiochem
3. HEPES: Calbiochem
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: αvβ3 was purified from 293 cells overexpressing αvβ3 (Duong et al., *J. Bone Min. Res.*, 8:S378, 1993) according to Pytela (Methods in Enzymology, 144:475, 1987)
12. Binding buffer: 50 mM HEPES, pH 7.8, 100 mM NaCl, 1 mM $Ca^{2+}/Mg^{230}$, 0.5 mM PMSF
13. 50 mM octylglucoside in binding buffer: 50-OG buffer

PROCEDURE

1. Pretreatment of SPA beads 500 mg of lyophilized SPA beads were first washed four times with 200 ml of 50-OG buffer and once with 100 ml of binding buffer, and then resuspended in 12.5 ml of binding buffer.

2. Preparation of SPA beads and receptor mixture

In each assay tube, 2.5 μl (40 mg/ml) of pretreated beads were suspended in 97.5 μl of binding buffer and 20 ml of 50-OG buffer. 5 ml (~30 ng/μl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.

3. Reaction

The following were sequentially added into Optiplate in corresponding wells:

(i) Receptor/beads mixture (75 µl)

(ii) 25 µl of each of the following: compound to be tested, binding buffer for total binding or A-8 for non-specific binding (final concentration 1 µM)

(iii) A-10 in binding buffer (25 µl, final concentration 40 pM)

(iv) Binding buffer (125 µl)

(v) Each plate was sealed with plate sealer from PACKARD and incubated overnight with rocking at 4° C.

4. Plates were counted using PACKARD TOPCOUNT

5.% inhibition was calculated as follows:

A=total counts

B=nonspecific counts

C=sample counts

% inhibition=[{(A-B)-(C-B)}/(A-B)]/(A-B)×100

OCFORM ASSAY

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 µL syringe with a 27.5 gauge needle. The marrow was suspended by pipetting up and down. The suspension was passed through >100 mm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1 \times 10^6$ cells/mL. 50 µL was added to each well of 1.8 cells to yield 50,000 cells/well and 1,25-dihydroxy-vitamin $D_3$ ($D_3$) was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing $D_3$. After an additional 48 h., the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS -Mx phosphate. After staining, the plates were washed extensively with deionized water and air dried. The number of multinucleated, positive staining cells was counted in each well.

SPAV5 ASSAY

MATERIALS

1. Wheat germ agglutinin Scintillation Proximity Beads (SPA): Amersham

2. Octylglucopyranoside and Phorbo-12-myristate-13-acetate (PMA):
   Calbiochem

3. Tris-HCl, NaCl and $CaCl_2$: Fisher

4. Minimum Essential Media (MEM): Gibco/BRL

5. Fetal bovine serum (FBS): Hyclone

6. $MgCl_2$, $MnCl_2$, and Phenylmethylsulfonylfluoride (PMSF): SIGMA

7. Protease inhibitor cocktail tablets: Boehringer Mannheim.

8. Optiplate-96 wells: PACKARD

9. B-5 was used as radiolabeled ligand (specific activity 500–1000 Ci/mmole) and B-3 (2.5 µM) was used to achieve 100% inhibition.

10. Test compound.

11. HEK293 cells overexpressing $\alpha_v\beta_5$ integrins (Simon et al., J. Biol. Chem. 272, 29380–29389, 1997) are cultured in 150 mm dishes in 10% FBS/MEM media (Gibco/BRL).

12. Lysis buffer: 100 mM octylglucopyranoside, 50 mM Tris, pH 7.5, 100 mM NaCl, 1 mM $CaCl_2$, 1 mM $MgCl_2$, 0.5 mM PMSF and protease inhibitors (1 tablet/50 ml buffer).

13. Binding buffer: 50 mM Tris, pH 7.5, 100 mM NaCl, 1 mM $CaCl_2$ 1 mM $MgCl_2$ and 1 mM $MnCl_2$.

14. 50 mM octylglucopyranoside in binding buffer: 50-OG buffer

PROCEDURE

1. $\alpha_v\beta_5$-cell lysates: HEK 293 cells expressing $\alpha_v\beta_5$ integrins were cultured until confluent. Cells were then starved overnight in media containing 0.5% FBS, followed by treatment with 100 nM PMA for 20 min. Cells were washed 2 times with cold phosphate buffer saline (4° C.) and solubilized in lysis buffer for 30 min on ice. Lysates were clarified using a Beckman JA-20 at 20,000 g. Protein concentration of clarified lysates was determined using a micro BCA kit (Pierce) and stored in aliquots at 80° C.

2. Pretreatment of SPA beads:

500 mg of lyophilized SPA beads were first washed four times with 200 ml of 50-OG buffer and once with 100 ml of binding buffer, and then resuspended in 12.5 ml of binding buffer.

3. Preparation of SPAV5 binding reaction

To each assay well, the following were sequentially added into Optiplate plates:

(i) Binding buffer to make up final volume of 125 µT per well. (ii) 3 µl (120 µg/well) of pretreated beads diluted with 22 µl of 50-OG Buffer (iii) 15 µg of $\alpha_v\beta_5$-cell lysate proteins.

(iv) B-5 at 50,000 cpm.

(v) 25 µl of graded concentrations of test compound.

(vi) Each plate was sealed with plate sealer from PACKARD and incubated overnight with rocking at 4° C.

4. Plates were counted using PACKARD TOPCOUNT microplate scintillation counter.

5.% Inhibition was calculated as follows:

A=total counts (binding of receptor to B-5)

B=nonspecific counts (binding of receptor to B-5 in the presence of 2.5 µM cold ligand)

C=counts from receptor binding to test compound

% inhibition=[{(A-B)-(C-B)}/(A-B)]×100

$IC_{50}$ of test compound was calculated as 50% of inhibition.

Representative compounds of the present invention were tested and found to bind to human αvµ3 integrin. These compounds were generally found to have $IC_{50}$ values less 50 nM in the SPAV3 assay.

Representative compounds of the present invention were also tested in the SPAV5 assay to determine affinity for the αvβ5 receptor. These compounds were generally found to have $IC_{50}$ values less than 100 nM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the Formula (I)

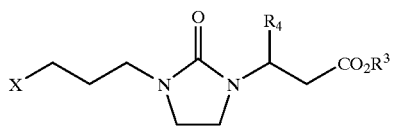

or a pharmaceutically acceptable salt thereof, wherein:

X is selected from the group consisting of

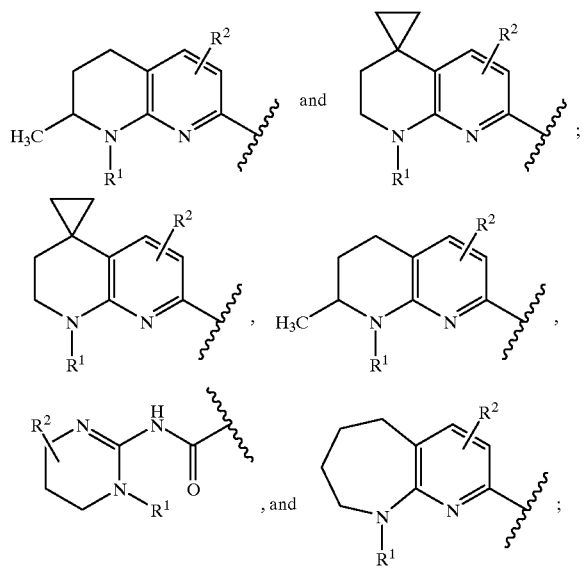

each $R^1$ is independently hydrogen or $C_{1-3}$ alkyl and each non-aromatic ring carbon atom is unsubstituted or independently substituted with one or two $R^2$ substituents and each aromatic ring carbon atom is unsubstituted or independently substituted with one $R^2$ substituent selected from the group consisting of $C_{1-8}$ alkyl, $C_{3-8}$ cycloalkyl, $C_{3-8}$ cycloheteroalkyl, $C_{3-8}$ cycloalkyl-$C_{1-6}$ alkyl, $C_{3-8}$ cycloheteroalkyl-$C_{1-6}$ alkyl, aryl, aryl-$C_{1-6}$ alkyl, amino-$C_{1-6}$ alkyl, $C_{1-3}$ acylamino, $C_{1-3}$ acylamino-$C_{1-6}$ alkyl, amino, $(C_{1-6}$ alkyl$)_{1-2}$ amino, $C_{3-6}$ cycloalkyl-$C_{0-2}$ amino, $(C_{1-6}$ alkyl$)_{1-2}$ amino-$C_{1-6}$ alkyl, $C_{1-6}$ alkoxy, $C_{1-4}$ alkoxy-$C_{1-6}$ alkyl, hydroxycarbonyl, hydroxycarbonyl-$C_{1-6}$ alkyl, $C_{1-3}$ alkoxycarbonyl, $C_{1-3}$ alkoxycarbonyl-$C_{1-6}$ alkyl, hydroxy, hydroxy-$C_{1-6}$ alkyl, nitro, cyano, trifluoromethyl, trifluoromethoxy, trifluoroethoxy, $C_{1-8}$ alkyl-S(O)$_{0-2}$, $(C_{1-8}$ alkyl$)_{0-2}$ aminocarbonyl, $C_{1-8}$ alkyloxycarbonylamino, $(C_{1-8}$ alkyl$)_{1-2}$ aminocarbonyloxy, (aryl)$_{1-2}$ amino, aryl-$C_{1-3}$ alkylsulfonylamino, and $C_{1-8}$ alkylsulfonylamino;

or two $R^2$ substituents, when on the same non-aromatic carbon atom, are taken together with the carbon atom to which they are attached to form a carbonyl group; or two $R^2$ substituents, together with the carbon atom to which they are attached, join to form a 3- to 6-membered saturated spiro-carbocyclic ring;

$R^4$ is aryl wherein the aryl group is selected from the group consisting of (1) phenyl,
(2) naphthyl,
(3) pyridyl,
(4) furyl,
(5) thienyl,
(6) pyrrolyl,
(7) oxazolyl,
(8) thiazolyl,
(9) imidazolyl,
(10) pyrazolyl,
(11) isoxazolyl,
(12) isothiazolyl,
(13) pyrimidinyl,
(14) quinolyl,
(15) isoquinolyl,
(16) benzimidazolyl,
(17) benzofuryl,
(18) benzothienyl,
(19) indolyl,
(20) benzthiazolyl,
(21) benzoxazolyl,
(22) dihydrobenzofuryl,
(23) benzo(1,3)dioxolanyl, and
(24) benzo(1,4)dioxanyl;

and mono, di, and tri-substituted aryl wherein the substituents are independently hydrogen, hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino-$C_{1-6}$ alkyl, di($C_{1-6}$)alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl-$C_{1-6}$ alkyl, $C_{1-5}$ alkylcarbonyloxy, cyano, trifluoromethyl, 1,1,1-trifluoroethyl, trifluoromethoxy, trifluoroethoxy, or nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl; and $R^3$ is hydrogen or $C_{1-3}$ alkyl.

2. The compound of claim 1 wherein $R^4$ is mono- or di-substituted phenyl, pyridyl, quinolyl, pyrimidinyl, pyrazolyl, or dihydrobenzofuryl;

wherein the substituents are independently hydrogen, hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino-$C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino $C_{1-6}$ alkyl, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl $C_{1-6}$ alkyl, $C_{1-5}$ alkylcarbonyloxy, cyano, trifluoromethyl, 1,1,1-trifluoroethyl, trifluoromethoxy, trifluoroethoxy, or nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl.

3. The compound of claim 2 wherein $R^4$ is mono- or di-substituted quinolyl, pyridyl, or pyrimidinyl;

wherein the substituents are independently hydrogen, halogen, phenyl, $C_{1-4}$ alkyl, $C_{3-6}$ cycloalkyl, $C_{1-3}$ alkoxy, amino, $C_{1-3}$ alkylamino, di($C_{1-3}$) alkylamino, hydroxy, cyano, trifluoromethyl, 1,1,1-trifluoroethyl, trifluoromethoxy, or trifluoroethoxy.

4. The compound of claim 3 wherein $R^2$ is selected from the group consisting of $C_{1-4}$ alkylamino, $C_{3-6}$ cycloalkyl-$C_{0-2}$ alkylamino cyano, $C_{1-4}$ alkyl, cyclopropyl, aryl $C_{1-3}$ alkyl, $C_{1-4}$ acylamino, $C_{1-4}$ alkoxy, $C_{1-4}$ alkylthio, aminocarbonyl, ($C_{1-6}$ alkyl)$_{1-2}$ aminocarbonyl, $C_{1-4}$ alkoxycarbonyl, trifluoromethyl, and trifluoromethoxy.

5. The compound of claim 4 wherein $R^2$ is selected from the group consisting of $C_{1-3}$ alkylamino, $C_{3-6}$ cycloalkylmethylamino, $C_{1-4}$ alkyl, cyclopropyl, trifluoromethyl, and trifluoromethoxy.

6. The compound of claim 5 selected from the group consisting of:

3-(6-methoxy-pyridin-3-yl)-3-{2-oxo-3-(5,6,7,8-tetrahydro-5,5-ethyleno- [1,8]naphthyridin-2-yl)-propyl]-imidazolidin-1-yl-propionic acid;

3(R)-(6-methoxy-pyridin-3-yl)-3-{2-oxo-3-(5,6,7,8-tetrahydro-5,5-ethyleno- [1,8]naphthyridin-2-yl)-propyl]-imidazolidin-1-yl-propionic acid;

3(S)-(6-methoxy-pyridin-3-yl)-3-{2-oxo-3-(5,6,7,8-tetrahydro-5,5-ethyleno- [1,8]naphthyridin-2-yl)-propyl]-imidazolidin-1-yl-propionic acid;

3(S)-(6-Methoxy-pyridin-3-yl)-3-{2-oxo-3-(7(R)-methyl-5,6,7,8-tetrahydro- [1,8]naphthyridin-2-yl)-propyl]-imidazolidin-1-yl}-propionic acid; and 3(S)-(6-Methoxy-pyridin-3-yl)-3-{2-oxo-3-(7(S)-methyl-5,6,7,8-tetrahydro- [1,8]naphthyridin-2-yl)-propyl]-imidazolidin-1-yl}-propionic acid;

or a pharmaceutically acceptable salt thereof.

7. A pharmaceutical composition comprising a compound according to claim 1 and a pharmaceutically acceptable carrier.

8. The composition of claim 7 which further comprises an active ingredient selected from the group consisting of a) an organic bisphosphonate or a pharmaceutically acceptable salt or ester thereof, b) an estrogen receptor modulator, c) an androgen receptor modulator, d) a cytotoxic/antiproliferative agent, e) a matrix metalloproteinase inhibitor, f) an inhibitor of epidermal-derived, fibroblast-derived, or platelet-derived growth factors, g) an inhibitor of VEGF, h) an antibody to a growth factor or a growth factor receptor, i) an inhibitor of Flk-1/KDR, Flt-1, Tck/Tie-2, or Tie-1, j) a cathepsin K inhibitor, k) a growth hormone secretagogue, l) an inhibitor of osteoclast proton ATPase, m) an inhibitor of urokinase plasminogen activator, n) a tumor-specific antibody-interleukin-2 fusion protein, o) an inhibitor of HMG-CoA reductase, p) a farnesyl transferase inhibitor or a geranylgeranyl transferase inhibitor or a dual farnesyl/geranylgeranyl transferase inhibitor, and q) human parathyroid hormone (hPTH) or hPTH(1-34);

and mixtures thereof.

9. The composition of claim 8 wherein said active ingredient is selected from the group consisting of a) an organic bisphosphonate or a pharmaceutically acceptable salt or ester thereof, b) an estrogen receptor modulator, c) an androgen receptor modulator, d) a cathepsin K inhibitor, e) an HMG-CoA reductase inhibitor, and f) an inhibitor of osteoclast proton ATPase;

and mixtures thereof.

10. The composition of claim 9 wherein said organic bisphosphonate or pharmaceutically acceptable salt or ester thereof is alendronate monosodium trihydrate.

11. A method of treating or preventing osteoporosis in a mammal in need thereof, comprising administering to the mammal a therapeutically effective amount of a compound according to claim 1.

12. A method of inhibiting a condition selected from the group consisting of bone resorption, restenosis, angiogenesis, biabetic retinopathy, macular degeneration, and inflammatory arthritis, comprising administering to a mammal in need thereof a therapeutically effective amount of a compound according to claim 1.

13. A method of treating or preventing osteoporosis which comprises administering to a mammal in need of such treatment or prevention a therapeutically or prophylactically effective amount of a compound of claim 1 in combination with an effective amount of an organic bisphosphonate or a pharmaceutically acceptable salt or ester thereof.

14. The method of claim 13 wherein said organic bisphosphonate or pharmaceutically acceptable salt or ester thereof is alendronate monosodium trihydrate.

* * * * *